US006489346B1

(12) United States Patent
Phillips

(10) Patent No.: US 6,489,346 B1
(45) Date of Patent: *Dec. 3, 2002

(54) SUBSTITUTED BENZIMIDAZOLE DOSAGE FORMS AND METHOD OF USING SAME

(75) Inventor: Jeffrey Owen Phillips, Ashland, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/481,207

(22) Filed: Jan. 11, 2000

Related U.S. Application Data

(63) Continuation-in-part of application No. 09/183,422, filed on Oct. 30, 1998, now abandoned, which is a continuation-in-part of application No. 08/680,326, filed on Jul. 15, 1996, now Pat. No. 5,840,737

(60) Provisional application No. 60/009,608, filed on Jan. 4, 1996.

(51) Int. Cl.[7] .................. C07D 401/12; A61K 31/4439
(52) U.S. Cl. .................... 514/338; 514/395; 546/273.7; 548/307.1
(58) Field of Search ................................ 514/338, 395; 546/273.7; 548/307.1

(56) References Cited

U.S. PATENT DOCUMENTS

| | | |
|---|---|---|
| 4,045,564 A | 8/1977 | Berntsson et al. |
| 4,182,766 A | 1/1980 | Krasso et al. |
| 4,255,431 A | 3/1981 | Junggren et al. |
| 4,337,257 A | 6/1982 | Junggren et al. |
| 4,359,465 A | 11/1982 | Ruwart |
| 4,414,216 A | 11/1983 | Kawakita et al. |
| 4,472,409 A | 9/1984 | Senn-Bilfinger |
| 4,508,905 A | 4/1985 | Junggren et al. |
| 4,544,750 A | 10/1985 | Brandstorm et al. |
| 4,620,008 A | 10/1986 | Brandstrom et al. |
| 4,636,499 A | 1/1987 | Brandstrom et al. |
| 4,725,691 A | 2/1988 | Brandstrom et al. |
| 4,738,974 A | 4/1988 | Brandstrom et al. |
| 4,786,505 A | * 11/1988 | Lovgren et al. ............ 514/338 |
| 4,853,230 A | 8/1989 | Lovgren et al. |
| 4,965,351 A | 10/1990 | Caruso et al. |
| 4,985,548 A | 1/1991 | Caruso et al. |
| 5,008,278 A | 4/1991 | Brandstrom et al. |
| 5,013,743 A | 5/1991 | Iwahi et al. |
| 5,019,584 A | 5/1991 | Brandstrom et al. |
| 5,025,024 A | 6/1991 | Brandstrom et al. |
| 5,039,806 A | 8/1991 | Brandstrom et al. |
| 5,045,321 A | 9/1991 | Makino et al. |
| 5,075,323 A | 12/1991 | Fain et al. |
| 5,093,132 A | 3/1992 | Makino et al. |
| 5,093,342 A | 3/1992 | Tomoi et al. |
| 5,106,862 A | 4/1992 | Briving et al. |
| 5,124,158 A | 6/1992 | Ruwart et al. |
| 5,215,974 A | 6/1993 | Alminger et al. |
| 5,219,870 A | 6/1993 | Kim |
| 5,232,706 A | 8/1993 | Coll |
| 5,244,670 A | 9/1993 | Upson et al. |
| 5,288,506 A | 2/1994 | Spickett et al. |
| 5,339,700 A | 8/1994 | Wright et al. |
| 5,374,730 A | 12/1994 | Slemon et al. |
| 5,385,739 A | 1/1995 | Debregeas et al. |
| 5,386,032 A | 1/1995 | Brandstrom |
| 5,391,752 A | 2/1995 | Hoerrner et al. |
| 5,395,323 A | 3/1995 | Berglund |
| 5,399,700 A | 3/1995 | Min et al. |
| 5,417,980 A | 5/1995 | Goldman et al. |
| 5,430,042 A | 7/1995 | Lindberg et al. |
| 5,447,918 A | 9/1995 | McCullough |
| 5,447,923 A | 9/1995 | Castrenich et al. |
| 5,470,983 A | 11/1995 | Slemon et al. |
| 5,504,082 A | 4/1996 | Kawakita et al. |
| 5,589,491 A | 12/1996 | Nakanishi et al. |
| 5,599,794 A | 2/1997 | Eek et al. |
| 5,629,305 A | 5/1997 | Eek et al. |
| 5,633,244 A | 5/1997 | Eek et al. |
| 5,639,478 A | 6/1997 | Makino et al. |
| 5,690,960 A | 11/1997 | Bengtsson et al. |
| 5,693,818 A | 12/1997 | Von Unge |
| 5,714,504 A | 2/1998 | Lindberg et al. |
| 5,714,505 A | 2/1998 | Hasselkus |
| 5,731,002 A | 3/1998 | Olovson et al. |
| 5,753,265 A | 5/1998 | Bergstrand et al. |
| 5,766,622 A | 6/1998 | Nelson |
| 5,776,765 A | 7/1998 | Graham et al. |

(List continued on next page.)

FOREIGN PATENT DOCUMENTS

| | | |
|---|---|---|
| CA | 1234118 | 3/1988 |
| DK | 19752843 | 7/1999 |
| EP | 0005129 | 10/1979 |
| EP | 0040639 | 12/1981 |
| EP | 0244380 | 11/1987 |

(List continued on next page.)

OTHER PUBLICATIONS

CA 119 :278792, Ooishi et al., 1993.*

(List continued on next page.)

Primary Examiner—Jane Fan
(74) Attorney, Agent, or Firm—Mayer, Brown, Rowe & Maw; Joseph A. Mahoney; Thomas R. Stiebel

(57) ABSTRACT

There is provided a solid pharmaceutical composition in a dosage form that is not enteric-coated, having active ingredients including a non-enteric coated proton pump inhibitor and at least one buffering agent. The proton pump inhibitor is omeprazole, lansoprazole, rabeprazole, esomeprazole, pantoprazole, paripprazole, and leminoprazole, or an enantiomer, isomer, derivative, free base, or salt thereof, in an amount of approximately 5 mg to approximately 300 mg; and the buffering agent is in an amount of approximately 0.1 mEq to approximately 2.5 mEq per mg of proton pump inhibitor. The dosage form includes a suspension tablet, a chewable tablet, an effervescent powder, or an effervescent tablet. Also provided is a method for treating an acid-related gastrointestinal disorder in a subject in need thereof by administering to the subject a solid pharmaceutical composition.

118 Claims, 2 Drawing Sheets

U.S. PATENT DOCUMENTS

| | | | |
|---|---|---|---|
| 5,798,120 A | 8/1998 | Tomohisa et al. |
| 5,814,338 A | 9/1998 | Veronesi |
| 5,817,338 A | 10/1998 | Bergstrand et al. |
| 5,840,737 A | 11/1998 | Phillips |
| 5,877,192 A | 3/1999 | Lindberg et al. |
| 5,879,708 A | 3/1999 | Makino et al. |
| 5,883,102 A | 3/1999 | Hamley et al. |
| 5,885,594 A | 3/1999 | Nilsen et al. |
| 5,900,424 A | 5/1999 | Kallstrom et al. |
| 5,929,244 A | 7/1999 | Von Unge |
| 5,939,091 A | 8/1999 | Eoga et al. |
| 5,948,789 A | 9/1999 | Larsson et al. |
| 5,955,107 A | 9/1999 | Augello et al. |
| 5,958,955 A | 9/1999 | Gustavsson et al. |
| 5,962,022 A | 10/1999 | Bolt et al. |
| 5,965,162 A | 10/1999 | Fuisz et al. |
| 5,972,389 A | 10/1999 | Shell et al. |
| 5,979,515 A | 11/1999 | Olsson |
| 6,013,281 A | 1/2000 | Lundberg et al. |
| 6,017,560 A | 1/2000 | Makino et al. |
| 6,090,827 A | 7/2000 | Erickson et al. |
| 6,123,962 A | 9/2000 | Makino et al. |
| 6,124,464 A | 9/2000 | Hogberg et al. |
| 6,132,770 A | 10/2000 | Lundberg |
| 6,132,771 A | 10/2000 | Depui et al. |
| 6,136,344 A | 10/2000 | Depui et al. |
| 6,143,771 A | 11/2000 | Lindberg et al. |
| 6,147,103 A | 11/2000 | Anousis et al. |
| 6,150,380 A | 11/2000 | Lovqvist et al. |
| 6,162,816 A | 12/2000 | Bohlin et al. |
| 6,166,213 A | 12/2000 | Anousis et al. |
| 6,183,776 B1 | 2/2001 | Depui et al. |
| 6,274,173 B1 | 8/2001 | Sachs et al. |
| 6,284,271 B1 | 9/2001 | Lundberg et al. |

FOREIGN PATENT DOCUMENTS

| | | |
|---|---|---|
| EP | 0247983 | 12/1987 |
| EP | 0308515 | 3/1989 |
| EP | 0315964 | 5/1989 |
| EP | 0394471 | 10/1990 |
| EP | 0414847 | 3/1991 |
| EP | 0436620 | 7/1991 |
| EP | 0452697 | 10/1991 |
| EP | 0465254 | 1/1992 |
| EP | 0237200 | 7/1992 |
| EP | 0496437 | 7/1992 |
| EP | 0502556 | 9/1992 |
| EP | 0338861 | 1/1993 |
| EP | 0248634 | 7/1993 |
| EP | 0565210 | 10/1993 |
| EP | 0567201 | 10/1993 |
| EP | 0567643 | 11/1993 |
| EP | 0587659 | 3/1994 |
| EP | 0652751 | 5/1995 |
| EP | 0654471 | 5/1995 |
| EP | 0696921 | 2/1996 |
| EP | 1004305 | 5/2000 |
| ES | 2024993 | 12/1990 |
| GB | 2189698 | 11/1987 |
| JP | 70039541 | 12/1970 |
| JP | 70039543 | 12/1970 |
| JP | 71009580 | 3/1971 |
| JP | 71009581 | 3/1971 |
| JP | 48103567 | 12/1973 |
| JP | 49005967 | 1/1974 |
| JP | 49013172 | 2/1974 |
| JP | 49020173 | 2/1974 |
| JP | 49020174 | 2/1974 |
| JP | 49093537 | 9/1974 |
| JP | 49095997 | 9/1974 |
| JP | 74041198 | 11/1974 |
| JP | 50052065 | 5/1975 |
| JP | 50112373 | 9/1975 |
| JP | 50142565 | 11/1975 |
| JP | 51016669 | 2/1976 |
| JP | 51131875 | 11/1976 |
| JP | 52005769 | 1/1977 |
| JP | 52014776 | 2/1977 |
| JP | 51017268 | 8/1977 |
| JP | 52097978 | 8/1977 |
| JP | 53059675 | 5/1978 |
| JP | 55019211 | 2/1980 |
| JP | 80019211 | 5/1980 |
| JP | 56061311 | 5/1981 |
| JP | 59095997 | 6/1984 |
| JP | 61221117 | 10/1986 |
| JP | 62145083 | 6/1987 |
| JP | 62258316 | 11/1987 |
| JP | 62258320 | 11/1987 |
| JP | 62277322 | 12/1987 |
| JP | 62283964 | 12/1987 |
| JP | 02022225 | 1/1990 |
| JP | 03163018 | 11/1990 |
| JP | 03034967 | 2/1991 |
| JP | 03048680 | 3/1991 |
| JP | 03052887 | 3/1991 |
| JP | 05117268 | 5/1993 |
| JP | 05194224 | 8/1993 |
| JP | 05194225 | 8/1993 |
| JP | 05255088 | 10/1993 |
| JP | 05294831 | 11/1993 |
| JP | 06092853 | 4/1994 |
| JP | 06100449 | 4/1994 |
| JP | 07033659 | 2/1995 |
| JP | 09087110 | 3/1997 |
| JP | 10017470 | 1/1998 |
| JP | 10017471 | 1/1998 |
| JP | 2000212180 | 8/2000 |
| KR | 9603605 | 3/1996 |
| KR | 9611238 | 8/1996 |
| KR | 9611390 | 8/1996 |
| RO | 88351 | 4/1986 |
| WO | 8900566 | 1/1989 |
| WO | 9204898 | 4/1992 |
| WO | 9208716 | 5/1992 |
| WO | 9305770 | 4/1993 |
| WO | 9400112 | 1/1994 |
| WO | 9402140 | 2/1994 |
| WO | 9402141 | 2/1994 |
| WO | 9501783 | 1/1995 |
| WO | 9507913 | 3/1995 |
| WO | 9515962 | 6/1995 |
| WO | 9523594 | 9/1995 |
| WO | 9532957 | 12/1995 |
| WO | 9532958 | 12/1995 |
| WO | 9532959 | 12/1995 |
| WO | 9601612 | 1/1996 |
| WO | 9601622 | 1/1996 |
| WO | 9601623 | 1/1996 |
| WO | 9601624 | 1/1996 |
| WO | 9601625 | 1/1996 |
| WO | 9602236 | 2/1996 |
| WO | 9616959 | 6/1996 |
| WO | 9624338 | 8/1996 |
| WO | 9624375 | 8/1996 |
| WO | 9638175 | 12/1996 |
| WO | 9709964 | 3/1997 |
| WO | 9725030 | 7/1997 |

| | | |
|---|---|---|
| WO | 9725064 | 7/1997 |
| WO | 9725065 | 7/1997 |
| WO | 9725066 | 7/1997 |
| WO | 9741114 | 11/1997 |
| WO | 9748380 | 12/1997 |
| WO | 9800114 | 1/1998 |
| WO | 9802368 | 1/1998 |
| WO | 9816228 | 4/1998 |
| WO | 9828294 | 7/1998 |
| WO | 9840054 | 9/1998 |
| WO | 9850019 | 11/1998 |
| WO | 9853803 | 12/1998 |
| WO | 9854171 | 12/1998 |
| WO | 9900380 | 1/1999 |
| WO | 9908500 | 2/1999 |
| WO | 9925323 | 5/1999 |
| WO | 9925711 | 5/1999 |
| WO | 9927917 | 6/1999 |
| WO | 9929299 | 6/1999 |
| WO | 9929320 | 6/1999 |
| WO | 9932091 | 7/1999 |
| WO | 9932093 | 7/1999 |
| WO | 9945004 | 9/1999 |
| WO | 9953918 | 10/1999 |
| WO | 9955705 | 11/1999 |
| WO | 9955706 | 11/1999 |
| WO | 0001372 | 1/2000 |
| WO | 0009092 | 2/2000 |
| WO | 0010999 | 3/2000 |
| WO | 0015195 | 3/2000 |
| WO | 0026185 | 5/2000 |
| WO | 0027366 | 5/2000 |
| WO | 0028975 | 5/2000 |
| WO | 0030612 | 6/2000 |
| WO | 0035448 | 6/2000 |
| WO | 0044744 | 8/2000 |
| WO | 0045817 | 8/2000 |
| WO | 0050038 | 8/2000 |
| WO | 0069438 | 11/2000 |
| WO | 0078293 | 12/2000 |
| WO | 0103707 | 1/2001 |
| WO | 0124780 | 4/2001 |
| WO | 0134573 | 5/2001 |

OTHER PUBLICATIONS

CA 123 :237886, McCullough, 1995.*

CA 123 :208914, Gergely et al., 1995.*

"Agents for Control of Gastric Acidity and Treatment of Peptic Ulcers", Chapter 37, pp. 907–909, 1768.

"Omeprazole, An Updated Review of its Pharmacology and Therapeutic Use in Acid–Related Disorders" by D. McTavish, et al., *Drugs*, vol. 42, No. 1, pp. 138–170 (1991).

"Omeprazole, Overview and Opinion" by S. Holt, et al., *Digestive Diseases and Sciences*, vol. 36, No. 4, pp. 385–393 (Apr. 1991).

"Pantoprazole, A Review of its Pharmacological Properties and Therapeutic Use in Acid–Related Disorders" by A. Fitton, et al., *Drugs*, vol. 51, No. 3, pp. 460–482 (Mar. 1996).

"Differential Stereoselective Pharmacolkinetics of Pantoprazole, a Proton Pump Inhibitor in Extensive and Poor Metabolizers of Pantoprazole—A Preliminary Study" by M. Tanaka, et al., *Chirality*, vol. 9, pp. 17–21 (1997).

"A Prospective Study of Simplified Omeprazole Suspension for the Prophylaxis of Stress–related Mucosal Damage" by J. Phillips, et al., *Critical Care Medicine*, vol. 24, No. 11, pp. 1793–1800 (1996).

"A Prospective Study of Omeprazole Suspension to Prevent Clinically Significant Gastrointestinal Bleeding From Stress Ulcers in Mechanically Ventilated Trauma Patients" by M. Lasky, et al., *The Journal of Trauma: Injury Infection, and Critical Care*, vol. 44, No. 3, pp. 527–533 (Mar. 1998).

"Effect of Combined Administration of Lansoprazole and Sofalcone on Microvascular and Connective Tissue Regeration After Ethanol–induced Mucosal Damage" by M. Nakamura, et al., *Journal of Clinical Gastroenterology*, vol. 27, Supp. 1, pp. 170–177 (1998).

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 [Date stamped in Howard University Library on Jan. 13, 1995].

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 (Jan. 1995). [Date stamped in Walter Reed Army Medical Center Medical Library on Jan. 17, 1995].

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 (Jan. 1995). [Date stamped in FDA Medical Library Jan. 6, 1995].

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 (Jan. 1995). [Date stamped in University of Illinois on Jan. 10, 1995].

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 (Jan. 1995). [Date stamped in Central DuPage Hospital Medical Library on Jan. 10, 1995].

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 (Jan. 1995). [Date stamped in University of Missouri Health Sciences Library Jan. 6, 1995].

"The Effect of Omeprazole/Sodium Bicarbonate Solution Administration on the Accuracy of Subsequent pH Measurements Through the Nasogastric Tube" by J. Whipple, et al., *Critical Care Medicine*, vol. 23, No. 1 Supplement, p. A69 (Jan. 1995). [Although allegedly date stamped in St. Vincent's Hospital Medical Library on Jan. 3, 1995, interviews of library personnel revealed that this Supplement was not received until Jan. 9, 1995, as the Jan. 9, 1995 date is found in their computerized database].

"Lansoprazole Capsules and Amoxicillin Oral Suspension in the Treatment of Peptic Ulcer Disease" by J. Hatlebakk, et al., *Scand. J. Gastroenterol.*, vol. 30, No. 11, pp. 1053–1057 (1995).

"Nicotinamide Pharmacokinetics in Humans: Effect of Gastric Acid Inhibition, Comparison of Rectal vs Oral Administration and the Use of Saliva for Drug Monitoring" by M.R. Stratford, et al. *J Cancer*, vol. 74, No. 1, pp. 16–21 (Jul. 1996).

"Comments of the Report of 'Association' of Omeprazole with DNA by Phillips, et al." by S.P. Adams *Mutagenesis*, vol. 7, No. 5, pp. 395–396 (Sep. 1992).

"Interaction of Omperazole with DNA in Rat Issues" by D.H. Phillips, *Mutagenesis*, vol. 7, No. 4, pp. 277–283 (Jul. 1992).

"Stability of Omeprazole in an Extemporaneously Prepared Oral Liquid" by R.A. Quercia, et al., *American Journal of Health–System Pharmacy*, vol. 54, pp. 1833–1836 (Aug. 15, 1997).

"Simplified Omeprazole Solution For The Prophylaxis of Stress–Related Mucosal Damage In Critically Ill Patients", by J. Phillips, et al., *Critical Care Medicine*, vol. 22, No. 1, p. A53 (Jan. 1994).

"Effective Gastric Acid Suppression After Oral Administration of Enteric–Coated Omeprazole Granules" by M.A. Mohiuddin, et al., *Digestive Diseases and Sciences*, vol. 42, No. 4, pp. 715–719 (Apr. 1997).

"Endoscopic Topical Therapy for the Treatment of Heliobacter Pylori Infection" by K. Kihira, et al. *J Gastroenterol*, vol. 31, Suppl 9, pp. 66–68 (Nov. 1996).

"Pharmacokinetic Evaluation of Omeprazole Suspension Following Oral Administration in Rats: Effect of Neutralization of Gastric Acid" by K. Watanabe, et al., *Acta Med Okayama*, vol. 50, No. 4, pp. 219–222 (Aug. 1996).

"Pharmacokinetics of Lansoprazole in Hemodialysis Patients" by M. Karol, et al., *J Clin Pharmacol*, vol. 35, pp. 815–820 (Aug. 1995).

"Omeprazole: Pharmacokinetics and Metabolism in Man" by C. Cederberg, et al., *Scand. J. Gastroenterol.*, vol. 24, Suppl. 166, pp. 33–40 (1989).

"Synthesis and Structure–Activity Relationships of Substituted 2–[2–imidazolylsulfinyl)methyl]Anilines As A New Class of Gastric H+/K(+)–ATPase Inhibitors. II." by T. Yamakawa, *Chem Pharm Bull* (Tokyo), vol. 40, No. 3, pp. 675–682 (Mar. 1992).

"Studies on (H(+)–K+)–ATPase Inhibitors of Gastric Acid Secretion. Prodrugs of 2–[(2–Pyridinylmethyl)sulfinyl]benzimidazole Proton–Pump Inhibitors" by J. Sih, et al., *Journal of Medicinal Chemistry*, vol. 34, No. 3, pp. 1049–1062 (Mar. 1991).

"Effects of Pantoprazole, A Novel H+/K+–ATPase Inhibitor, On Duodenal Ulcerogenic and Healing Responses in Rats: A Comparative Study with Omeprazole and Lansoprazole" by Takeuchi, et al., *J. Gastroenterol. Hepatol.*, vol. 14, No. 3, p. 251–57 (1999).

"Pharmacokinetics, Metabolism and Interactions of Acid Pump Inhibitors: Focus on Omeprazole, Lansoprazole and Pantoprazole" by T. Andersson, *Clin. Pharacokinet.*, vol. 31, No. 1, pp. 9–28 (Jul. 1996).

"Nasogastric Administration of Omeprazole", *The Australian Journal of Hospital Pharmacy*, vol. 28, No. 3, pp. 174–176 (1998).

"Bioavailability and Efficacy of Omeprazole Given Orally and By Nasogastric Tube" by C. Larson, et al., *Digestive Diseases and Sciences*, vol. 41, No. 3, pp. 475–479 (Mar. 1996).

"Nasogastic Omeprazole: Effects on Gastric pH in Critically Ill Patients" by D. Balaban, et al., *The American Journal of Gastroenterolgy*, vol. 92, No. 1, pp. 79–83 (1997).

"Comparison of 24–hour Intragastric pH Using Four Liquid Formulations of Lansoprazole and Omeprazole" by V. Sharma, *American Journal of Health–System Pharmacists*, vol. 56, Suppl 4, pp. S18–S21(Dec. 1, 1999).

"The Stability of Simplified Lansoprazole Suspension (SLS)" by J. Phillips, et al., *Gastroenterology*, vol. 116, No. 4, p. G0382 (Apr. 1999).

"Effect on 24–hour Intragastric Acidity of Simplified Omeprazole Solution (SOS) Administered Via Gastrostomy", by V. Sharma, et al., *AJG*, vol. 92, No. 9, p. 1625, Section 169 (1997).

"Simplified Lansoprazole Suspension (SLS): A Proton Pump Inhibitor (PPI) In A Liquid Formulation That Works" by V. Sharma, et al., *AJG*, p. 1647, Section 153 (Sep. 1998).

"Simplified Lansoprazole Suspension—A Liquid Formulation of Lansoprazole—Effectively Suppresses Intragastric Acidity When Administered Through a Gastrostomy" by V. Sharma, et al., *The American Journal of Gastroenterology*, vol. 94, No. 7, pp. 1813–1817 (Jul. 1999).

"The Effects on Intragastric Acidity of Per–Gastrostomy Administration of An Alkaline Suspension of Omeprazole" by V. Sharma, et al., *Aliment Pharmocol Ther*, vol. 13, pp. 1091–1095 (1999).

"A Multicenter, Prospective, Randomized Clinical Trial of Continuous Infusion I.V. Ranitidine vs. Omeprazole Suspension in the Prophylaxis of Stress Ulcers" by J. Phillips, et al., *Critical Care Medicine*, vol. 26, No. 1 (Suppl.), p. A101, No. 222 (1998).

"Gastrointestinal Drugs", *The American Medical Association Drug Evaluation*, vol. 2, The American Medical Association, Chicago, 1:8 (Bennett & Dickson, eds.).

"Pharmacokinetics of [$^{14}$C]Omeprazole in Patients with Liver Cirrhosis" by T. Andersson, et al., *Clin Pharmacokinet.*, vol. 24, No. 1, pp. 71–78 (1993).

"Pharmacokinetics and Bioavailability of Omeprazole After Single and Repeated Oral Administration in Healthy Subjects" by T. Andersson, et al., *Br. J. Clin. Pharmac.*, vol. 29, pp. 557–563 (1990).

"Development of An Oral Formulation of Omeprazole" by A. Pilbrant, et al., *Scand. J. Gastrolenterol*, vol. 20, (Suppl. 108) pp. 113–120 (1985).

"Pharmacokinetics of Various Single Intravenous and Oral Doses of Omeprazole" by T. Andersson, et al., *European Journal of Pharmacology*, vol. 39, pp. 195–197 (1990).

"Pharmacokinetic Study of Omeprazole in Elderly Healthy Volunteers" by S. Landahl, et al., *Clin. Pharmacokinet.*, vol. 23, No. 6, pp. 469–476 (1992).

"The Pharmacokinetics of Omeprazole in Humans—A Study of Single Intravenous and Oral Doses" by C. Regardh, et al., *Therapeutic Drug Monitoring*, vol. 12, No. 2, pp. 163–172 (1990).

"Bolus or Intravenous Infusion of Rantidine: Effects on Gastric pH and Acid Secreation" by Ballesteros, et al., *Ann. Intern. Med.*, vol. 112, pp. 334, 339 (1990).

"Therapeutic Use of Omeprazole For Refractory Stress–Induced Gastric Mucosal Hemorrage" by Barie & Hariri, *Critical Care Medicine*, vol. 20, pp. 899–901 (1992).

"Let's Agree on Terminology: Definition of Sepsis" by Bone, *Crictictical Care Medicine*, vol. 19, p. 27 (1991).

"Antacids vs. Sucralfate in Preventing Acute Gastrointestinal Tract Bleeding in Abdominal Aortic Surgery" by Borrero, et al., *Arch. Surg.*, vol. 121, pp. 810–812 (1986).

*The Pharmacologic Basis of Therapeutics* by Brunton, p. 907 (1990).

"Central Nervous System Reactions to Histamine–2 Receptor Blockers" by Cantu & Korek, vol. 114, pp. 1027–1034 (1994).

"Comparison of Acid Neutralizing and Non–acid Neutralizing Stress Ulcer Prophylaxis in Thermally Injured Patients" by Cioffi, et al., vol. 36, pp. 541–547 (1994).
"Risk Factors For Gastrointestinal Bleeding in Critically III Patients" by Cook, et al., vol. 330, pp. 377–381 (1994).
"Stress Ulcer Prophylaxis in the Critically Ill: A Meta Analysis" by Cook, et al., vol. 91, pp. 519–527 (1991).
"Nasocomial Pneumonia and the Role of Gastric pH: A Meta Analysis" by Cook, et al., vol. 100, pp. 7–13 (1991).
"Acute Gastroduodenal Disease After Themal Injury: An Endoscopic Evaluation of Incidence and Natural History" by Czaja, et al., vol. 291, pp. 925–929 (1974).
"Does pH Paper Accurately Reflect Gastric pH?" by Dobkin, et al., vol. 18, pp. 985–988 (1990).
"Nosocomial Pneumonia in Intubated Patients Given Sucralfate As Compared With Antacids or Histamine Type 2 Blockers" by Driks et al., *N. Eng. J. Med.*, vol. 317, pp. 1376–1382 (1987).
"Prospective Trial Comparing a Combination pH Probe–Nasogastric Tube With Aspirated Gastric pH" by Eisenberg, et al., *Critical Care Medicine*, vol. 18, 1092–95 (1990).
"Pneumonia and Stress Ulceration in Severely Injured Patients" by Fabian et al., vol. 128, p. 1855 (1993).
"Substituted Benzimidazoles Inhibit Gastric Acid Secretions by Blocking H+/K+–ATPase" by Fellenius, et al., *Nature*, vol. 290, pp. 159–161 (1981).
Predictive Value of Intramural pH and Other Risk Factors For Massive Bleeding From Stress Ulceration by Fiddian–Green, et al., *Gastroenterology*, vol. 8, pp. 613–620 (1983).
"Function and Structure of Parietal Cells After H+/K+–ATPase Blockade" by Fryklund, et al., *Am. J. Physiol.*, vol. 254, pp. G399–407 (1988).
"Thrombocytopenia Associated with Hypersensitivity to Rantidine: Possible Cross–Reactivity" by Gafter, et al., vol. 64, pp. 560–562 (1989).
"CDC Definitions for Nosocomial Infections" by Garner, et al., *Am. J. Infect. Control*, vol. 16, pp. 128–140 (1988).
"Intragastric pH Measurement Using a Novel Disposable Sensor" by Heath, et al., *Intes. Care Med.*, vol. 14, pp. 232–235 (1988).
"Effect of intravenous Infusion of Omeprazole and Rantidine on Twenty–Four–Hour Intragastric pH" by Kiilerich, et al., vol. 56, pp. 25–30 (1995).
"Prevention of Upper Gastrointestinal Bleeding in Long Term Ventilated Patients" by Laggner, et al., *Am. J. Med.*, vol. 86, Suppl. 6A, pp. 81–84 (1989).
"Gastric Response to Severe Head injury" by Larson, et al., *Am. J. Surg.*, vol. 147, pp. 97–105 (1984).
"Pathogenesis, Diagnosis and Treatment of Acute Gastric Mucosa Lesions" by Marrone & Silen, *Clin. Gastroenterol.*, vol. 13, pp. 635–650 (1984).
"Continuous Intravenous Cimetidine Decreases Stress–Related Upper Gastrointestinal Hemorrhage" by Martin, et al., *Critical Care Medicine*, vol. 21, pp. 19–39 (1993).
"Evaluation of Various Techniques to Monitor Intragastric pH" by Meiners et al., *Arch. Surg.*, vol. 117, pp. 288–291 (1982).
"Electrolyte and Acid–base Disorders" by Oh & Carroll, *The Pharmacologic Approach to the Critically Ill Patient*, pp. 966–967 (Chernow, B. ed. 1994).
"Control of Gastric pH With Cimetidine Boluses Versus Primed Infusions" by Ostro et al., *Gastroenterology*, vol. 89, pp. 532–537 (1985).

"Cimetidine for Prevention and Treatement of Gastroduodenal Mucosal Lesions in Patients" by Peura & Johnson, *Ann. Intern. Med.*, vol. 103, pp. 173–177 (1985).
"Occurrence of Nasocomial Pneumonia in Mechanically Ventilated Trauma Patients" by Pickworth, et al., *Critical Care Medicine*, vol. 12, pp. 1856–1862 (1993).
"Methods of Prophylaxis in Stress Ulcer Disease" by Priebe & Skillman, *World J. Surg.*, vol. 5, pp. 223–233 (1981).
"Nasocomial Pneumonia During Stress Ulcer Prophylaxis With Cimetidine and Sucralfate" by Ryan, et al., *Arch. Surg.*, vol. 128, pp. 1353–1357 (1993).
"Clinically Important Adverse Effects and Drug Interactions With H2–receptor Antagonists: An Update" by Sax, *Pharmacotherapy*, vol. 7, pp. 110S–115S (1987).
"Stress Ulcer Prophylaxis: Still a Valid Option in the 1990s?" by Schepp, vol. 54, pp. 189–199 (1993).
"Prophylactic Therapy for Acute Ulcer Bleeding: A Reappraisal" by Schuman, et al., *Ann. Intern. Med.*, vol. 106, pp. 562–567 (1987).
"Stress Ulcer Prophylaxis: In Whom? With What?" by Schuster, *Critical Care Medicine*, vol. 21, pp. 4–6 (1993).
"A Dosage Alternative for H–2 Receptor Antagonists, Continuous–Infusion" by Siepler, *Clin. Ther.*, vol. 8, pp. 24–33 (1986).
"Role of Gastric Colonizmation in the Development of Pneumonia in Critically Ill Trauma Patients" by Simms, et al., *J. Trauma*, vol. 31, pp. 531–536 (1991).
"Respiratory Failure, Hypotension, Sepsis and Jaundice: A Clinical Syndrome Associated With Lethal . . . " by Skillman, et al., *Am. J. Surg.*, vol. 117, pp. 523–530 (1969).
"The Gastric Mucosal Barrier: Clinical and Experimental Studies in Critically Ill and Normal Man . . . " by Skillman, et al., *Ann. Surg.*, vol. 172, pp. 564–584 (1970).
"Changing Perspectives of Stress Gastritis Prophylaxis" by Smythe & Zarowitz, *Ann. Pharmacother.*, vol. 28, pp. 1073–1084 (1994).
"Thrombocytopenia Associated With Rantidine" by Spychal & Wickman, *Br. Med. J.*, vol. 291, p. 1687 (1985).
"Stress Ulcer Prophylaxis—Quo Vadis?"by Tryba, *Intens. Care Med.*, vol. 20, pp. 311–313 (1994).
"Risk of Acute Stress Bleeding and Nosocomial Pneumonia in Ventilated Intensive Care patients. Sucralfate vs. Antacids" by Tryba, *Am. J. Med.*, vol. 87 (3B) 117–24 (1987).
"Side Effects of Ranitidine" by Vial, et al., *Drug Saf.*, vol. 6, pp. 94–117 (1991).
"The Relationship Between Gastric Acid Secretion and Gastric H+/K+–ATPase Activity" by Wallmark, et al., *J. Biol. Chem.*, vol. 260, pp. 13681–84 (1985).
"Tolerance During Dosing with H2 Receptor Antagonists: An Overview" by Wilder–Smith & Merki, *Scand. J. Gastroenterol.*, vol. 27, Suppl. 193, pp. 14–19 (1992).
"The Prevention of Gastro–Intestinal Tract Bleeding in Patients in an Intensive Care Unit" by Zinner, et al., *Surg. Gynecol. Obstet.*, vol. 153, pp. 214–220 (1981).
"Influence of Insulin Antibodies on Pharmacokinetics and Bioavailability of Recombinant Human . . . " by Gray, et al., *British Med. J.*, vol. 290, pp. 1687–1690 (1985).
"Nasogastric Administration of Omeprazole for Control of Gastric pH" by M. Carroll, et al., $10^{th}$ *World Congresses of Gastroenterology*, Abstracts (Oct. 2–7, 1994).
"A Lansoprazole Suspension Formulation As An Alternative to Capsules for Oral Administration" by S. Lockhart, et al., *World Congresses of Gastroenterology*, Abstract Exh A2074 (Sep. 6–11, 1998).

"Gastric Acid Antisecretory Effect of Two Different Dosage Forms of Omeprazole During Prolonged Oral Treatment in the Qastric Fistula Dog" by Larsson, et al., vol. 23, No. 8, pp. 1013–1019 (1988).

"Effect of Various Salts on the Stability of Lansoprazole, Omeprazole, and Pantoprazole as Determined by High–Performance Liquid Chromatography" by A. Ekpe, et al., *Drug Development and Industrial Pharmacy*, vol. 25, No. 9, pp. 1057–1065 (1999).

"Inhibition of Gastric Secretion by Omeprazole and Efficacy of Calcuim Carbonate in the Control of Hyperphosphatemia in Patients on Maintenance Hemodialysis" by Sechet, et al., *Nephrologie*, vol. 20, No. 4, pp. 213–216 (1999).

"Role of the Time of Administration of Calcium Carbonate in the Control of Hyperphophatemia in Patients on Maintenance Hemodialysis" by Sechet, et al., *Nephrologie*, vol. 20, No. 4, pp. 209–212 (1999).

Onset of Action of Antisecretory Drugs: Beneficial Effects of a Rapid Increase in Intragastric pH in Acid Reflux Disease by Pipkin, et al, *Scand. J. Gastroenterol. Supp.*, vol. 230, pp. 3–8 (1999).

"Omeprazole Disposition in Humans" by Regardh, et al., *Ther. Drug. Monit.*, vol. 12, No. 2, pp. 165 (1990).

"Evaluation of Buffering Capacity and Acid Neutralizing pH Time Profile of Antacids" by M. Lin, et al., *J Formos Med Assoc*, vol. 97, No. 10, pp. 704–710 (1998).

"A Study of Antacid Buffers: I. The Time Factor in Neutralization of Gastric Acidity", by J. Holbert, et al., *Journal of The American Pharmaceutical Association (Scientific Edition)*, vol. 36, pp. 149–151 (1947).

"Buffered and Isotonic Solutions", *Physical Pharmacy*, Chapter 8, pp. 169–189.

"Influence of Insulin Antibodies on Pharmacokinetics and Bioavailability of Recombinant Human . . . " by Gray, et al., *British Medical Journal*, 290: 1687–1690 (1985).

"Inhibition of Basal and Betazole—and Sham–Feeding–Induced Acid Secretion by Omeprozole in Man" by Lind, et al., *Scand. J. Gastroenterol*, 21:1004–1010 (1986).

"Lansoprazole: Phase I Study of Lansoprazole (AG–1749) Antiulcer Agent (Tablet Form)" by A. Nakagawa, et al., pp. 33–34 (1991).

"Pantoprozole Bicarbonate Suspension (PBS) Provides Oral Bioavailability Comparable To Tablet" by J. Paul, et al., *Critical Care Medicine*, (Feb. 2001).

*Physical Pharmacy—Physical Chemicals Principles in the Pharmaceutical Sciences*, Fourth Edition, by A. Martin, et al. (1993).

"Journal of Clinical Therapeutics & Medicines" by Nakagawaa, et al., vol. 7, No. 1, pp. 33–50 (1191).

Organic Chemistry by Wade, Pritice–Hall, Inc., p. 349 (1987).

"The Effect of Omeprazole/Sodium Bicarbonate Solution Administration on the Accuracy of Subsequent pH Measurements Through the Nasogastric Tube" by J. Whipple, et al., vol. 28, No. 1 (Suppl), p. A69 (Jan. 1995).

"High Acid Buffering Capacity of Protein Hydrolysate Infant Formulas" by I. Korponay–Szabo, et al., *Journal of Pediatric Gastroenterology and Nutrition*, vol. 31, Supplement 2, Abstract 956 (Aug. 5–9, 2000).

"Esomeprazole" by C. Spencer, et al., *Drugs 2000*, vol. 60, No. 2, pp. 321–329 (Aug. 2000).

"Zollinger–Ellison Syndrome—Clinical Presentation in 261 Patients" by P. Roy, et al., *Medicine*, vol. 79, No. 6, pp. 349–411 (2000).

"Overuse of Proton Pump Inhibitors" by M. Naunton, et al., *Journal of Clinical Pharmacy and Therapeutics*, vol. 25, pp. 333–340 (2000).

"The Proton–Pump Inhibitors: Similarities and Differences" by J. Horn, *Clinical Therapeutics*, vol. 22, No. 3, pp. 266–280 (2000).

"Pantoprazole: A New Proton Pump Inhibitor" by P. Jungnickel, *Clinical Therapeutics*, vol. 22, No. 11, pp. 1268–1293 (2000).

"Rabeprazole for the Prevention of Pathologic and Symptomatic Relapse of Erosive or Ulcerative Gastroesophageal Reflux Disease" by A. Caos, et al., *The American Journal of Gastroenterology*, vol. 95, No. 11, pp. 3081–3088 (2000).

"The Stability of Simplified Omeprazole Suspension (SOS)" by J. Phillips, et al., *Critical Care Medicine*, vol. 26, No. 1 (Suppl.), p. A101, No. 221 (1998).

"A Multicenter Prospective, Randomized Clinical Trial of Continuous Infusion I.V. Ranitidine vs. Omeprazole Suspension in The Prophylaxis of Stress Ulcers" by J. Phillips, et al., *Critical Care Medicine*, vol. 26, No. 1 (Suppl.) p. A101, No. 222 (1998).

(Deleted).

Sharma, et al., "Oral Pharmacokinetics of Omerprazole and Lansoprazole After Single and Repeated Doses as intact Capsules or As Suspensions in Sodium Bicarbonate", *Alimentary Pharmacology & Therapeutics*, vol. 14, No. 7, pp. 887–892 (Jul. 2000).

McAndrews, et al., "Omeprazole and Lansoprazole Suspensions for Nasogastric Administration", *American Journal of Health–System Pharm.*, vol. 56, p. 81 (Jan. 1, 1999).

Hardy, et al., "Inhibition of Gastric Secretion by Omeprazole and Efficiency of Calcium Carbonate on the Control of Hyperphosphatemia in Patients on Chronic Hemodialysis", *Artificial Organs*, vol. 22, No. 7, pp. 569–573 (Jul. 1998).

Schmassmann, et al., "Antacid Provides Better Restoration of Glandular Structures Within the Gastric Ulcer Scar Than Omeprazole", *Gut*, vol. 35, No. 7, pp. 896–904 (Jul. 1994).

Di Iorio, et al., "Aluminum and Phosphorus Urinary Excretion After Modifying Gastric Acid Secretion In Chronic Renal Failure", *Trace Elements and Electrolytes*, vol. 13, No. 2, pp. 96–101 (1996).

Di Iorio, et al., "Aluminum and Phosphorus Urinary Excretion After Modifying Gastric Acid Secretion In Normal Subjects", *Trace Elements and Electrolytes*, vol. 13, No. 1, pp. 47–49 (1996).

Osler, et al., "Effect of Omeprazole On The Phosphate–Binding Capacity of Calcium Carbonate", *Nephron*, vol. 69, pp. 89–90 (1995).

Schmassmann, et al., "Antacids in Experimental Gastric Ulcer Healing: Pharmacokinetics of Aluminum and Quality of Healing", *European Journal of Gastroenterology & Hepatology*, vol. 5, Suppl. 3, pp. S111–S116 (1993).

Humphries, et al., "Review Article: Drug Interactions With Agents Used to Treat Acid–Related Diseases", *Alimentary Pharmacology & Therapeutics*, vol. 13, Suppl. 3, pp. 18–26 (Aug. 1999).

Crill, et al., "Upper Gastrointestinal Tract Bleeding in Critically III Pediatric Patients", *Pharmacotherapy*, vol. 19, No. 2, pp. 162–180 (Feb. 1999).

Vincent, et al., "Concurrent Administration of Omeprazole and Antacid Does Not Alter The Pharmacokinetics and Pharmacodynamics Of Dofetilide in Healthy Subjects", *Clinical Pharmacology & Therapeutics*, vol. 59, No. 2 (PII–93), p. 182 (Feb. 1996).

Ching, et al., "Antacids—Indications and Limitations", *Drugs*, vol. 47, No. 2, pp. 305–317 (Feb. 1994).

Garnett, "Efficacy, Safety, and Cost Issues in Managing Patients With Gastroesophageal Reflux Disease", *Am. J. Hosp. Pharm.*, vol. 50, No. 4 (Suppl. 1), pp. S11–18 (Apr. 1993).

Hixson, et al., "Current Trends in the Pharmacotherapy for Peptic Ulcer Disease", *Arch. Intern. Med.*, vol. 152, No. 4, pp. 726–732 (Apr. 1992).

Hixson, et al., "Current Trends in the Pharmacotherapy for Gastroesophageal Reflux Disease", *Arch. Intern. Med.*, vol. 152, No. 4, pp. 717–723 (Apr. 1992).

Maxwell, et al., "Control of Gastric pH In A Critical Care Unit: Physician Behavior and Pharmacologic Effectiveness", *Am. Rev. Respir. Dis.*, vol. 143, No. 4 (Part 2), p. A482 (1991).

Siepler, et al., "Selecting Drug Therapy for Patients With Duodenal Ulcers", *Clinical Pharmacy*, vol. 9, No. 6, pp. 463–467 (Jun. 1990).

Rodrigo, et al., "Therapeutic Approach to Peptic Ulcer Relapse", *Methods Find Exp. Clinical Pharmacology*, vol. 11 (Supp. 1), pp. 131–135 (1989).

Deakin, et al., "Therapeutic Progress—Review XXXIII: Are We Making Progress In The Drug Treatment of Oesophageal Disease?", *Journal of Clinical Pharmacy and Therapeutics*, vol. 13, No. 6, pp. 365–374 (Dec. 1988).

Walan, "Pharmacological Agents For Peptic Ulcer Disease", *Scand. J. Gastroenterol. Suppl.*, vol. 19, No. 98, p. 1 (1984).

Al–Assi, et al., "Treatment of Helicobacter Pylori Infection With Omeprazole–Amoxicillin Combination Therapy Versus Ranitidine/Sodium Bicarbonate–Amoxicillin", *The American Journal of Gastroenterology*, vol. 90, No. 9, pp. 1411–1414 (Sep. 1995).

Tanaka, et al., "Pathogenesis of The Earliest Epithelial Cell Damage Induced by Mepirizole and Cysteamine in the Rat Duodenum", *Japanese Journal of Pharmacology*, vol. 51, No. 4, pp. 509–519 (Dec. 1989).

Yasuda, et al., "Antacids Have No Influence on the Pharmacokinetics of Rabeprazole, A New Proton Pump Inhibitor, In Healthy Volunteers", *International Journal of Clinical Pharmacology and Therapeutics*, vol. 37, No. 5, pp. 249–253 (1999).

Andersson, et al., "Pharmacokinetic Studies With Esomeprazole, the (S)–Isomer of Omeprazole", Clinical Pharmacokinetics, vol. 40, No. 6, pp. 411–426 (2001).

Maconi, et al., "Prolonging Proton Pump Inhibitor–Based Anti–Helicobacter Pylori Treatment From One to Two Weeks in Duodenal Ulcer: Is It Worthwhile?", *Digest Liver Disease*, vol. 32, pp. 275–280 (May 2000).

Doan, et al., "Comparative Pharmacokinetics and Pharmacodynamics of Lansoprazole Oral Capsules and Suspension in Healthy Subjects", *American Journal of Health–System Pharmacists*, vol. 58, No. 16, pp. 1512–1519 (Aug. 15, 2001).

Pilbrant, "Principles for Development of Antacids", *Scand. J. Gastroenterol Suppl.*, vol. 75, pp. 32–36 (1982).

DiGiacinto, et al., "Stability of Suspension Formulations of Lansoprazole and Omeprazole Stored in Amber–Colored Plastic Oral Syringes", *Annals of Pharmacotherapy*, vol. 34, No. 5, pp. 600–605 (May 2000).

Kromer, "Similarities and Differences in the Properties of Substituted Benzimidazoles: A Comparison Between Pantoprazole and Related Compounds", *Digestion*, vol. 56, No. 6, pp. 443–454 (1995).

Thomson, "Are The Orally Administered Proton Pump Inhibitors Equivalent? A Comparison of Lansoprazole, Omeprazole, Pantoprazole, and Rabeprazole", *Current Gastroenterology Reports*, vol. 2, No. 6, pp. 482–493 (Dec. 2000).

Cederberg, et al., "Effect of Once Daily Intravenous and Oral Omeprazole on 24–Hour Intragastric Acidity in Healthy Subjects", *Scand. J. Gastroenterol.*, vol. 28, No. 2, pp. 179–184 (Feb. 1993).

Sharma, et al., "The Pharmacodynamics of Lansoprazole Administered Via Gastrostomy as Intact, Non–Encapsulated Granules", *Alimentary Pharmacology Therapy*, vol. 12, pp. 1171–1174 (1998).

Regardh, et al., "Pharmacokinetics and Metabolism of Omeprazole in Animals and Man—An Overview", *Scand. J. Gastroenterology*, vol. 108, pp. 79–94 (1985).

Londong, et al., "Dose–Response Study of Omeprazole on Meal–Stimulated Gastric–Acid Secretion and Gastrin Release", *Gastroenterology*, vol. 85, No. 6, pp. 1373–1378 (1983).

Howden, et al., "Oral Pharmacokinetics of Omeprazole", *European Journal of Clinical Pharmacology*, vol. 26, pp. 641–643 (1984).

Prichard, et al., "Omeprazole: A Study of Its Inhibition of Gastric pH and Oral Pharmacokinetics After Morning Or Evening Dosage", Gastroenterology, vol. 88, Part 1, pp. 64–69 (1985).

Oosterhuis, et al. "Omeprazole: Pharmacology, Pharmacokinetics and Interactions", *Digestion*, vol. 44, Suppl. 1, pp. 9–17 (1989).

Arvidsson, et al., "Peak Distortion in the Column Liquid Chromatographic Determination of Omeprazole Dissolved in Borax Buffer", *Journal of Chromatography*, vol. 586, Part 2, pp. 271–276 (1991).

McAnderews, et al., "Alternative Method for Administering Proton–Pump Inhibitors Through Nasogastric Tubes", American Journal of Health–System Pharmacy, vol. 56 (May 15, 1999).

Poster presentation presented in Jan. 1994 by J. Phillips and M. Metzler at the Society for Critical Care Medicine Annual Meeting relating to SOS.

University of Missouri Surgical Society Scientific Program presented by J. Phillips entitled "Stress–Related Mucosal Damage Optimizing Drug Therapy in the 1990's" (Jun. 1994).

Presentation by J. Phillips entitled "Update on Acid–Related Disorders—Optimizing Pharmacotherapy for the 1990's" (1996).

Presentation by J. Phillips entitled "Stress–Related Mucosal Damage—Optimizing Drug Therapy" (1997).

Presentation by J. Phillips entitled "Overview of Omeprazole Suspension—From Efficacy to Effectiveness Alternative Dosing of PPI's" (Aug. 1998).

Presentation by J. Phillips entitled Simplified Omeprazole Suspension (SOS) (1998).

Presentation by J. Phillips entitled "Advances in the Use of PPI's From Efficacy to Effectiveness" (1999).

Presentation by J. Phillips entitled "Overview of Omeprazole Suspension—Problems With Administering Granules" (1999/2000).

Presentation on Overview of Omeprazole Suspension entitled "Pharmacotherapy Related Outcomes Group Researching Effective Stress Ulcer Strategies" (2000).

Presentation on Overview of Omeprazole Suspension entitled "Stress Ulcer Prophylaxis in the $21^{st}$ Century" (2001).

* cited by examiner

SUBSTITUTED BENZIMIDAZOLE DOSAGE FORMS AND METHOD OF USING SAME

This application is a continuation-in-part of U.S. patent application Ser. No. 09/183,422 filed on Oct. 30, 1998, now abandoned, which is a continuation-in-part of U.S. patent application Ser. No. 08/680,376 filed on Jul. 15, 1996, now U.S. Pat. No. 5,840,737, which claims priority to U.S. Provisional Application Serial No. 60/009,608 filed on Jan. 4, 1996. This application claims priority to all such previous applications, and such applications are hereby incorporated herein by reference.

TECHNICAL FIELD

The present invention relates to pharmaceutical preparations comprising substituted benzimidazole proton pump inhibitors.

BACKGROUND OF THE INVENTION

Omeprazole is a substituted benzimidazole, 5-methoxy-2-[(4-methoxy-3,5-dimethyl-2-pyridinyl)methyl]sulfinyl]-1H-benzimidazole, that inhibits gastric acid secretion. Omeprazole belongs to a class of antisecretory compounds called proton pump inhibitors ("PPIs") that do not exhibit anticholinergic or $H_2$ histamine antagonist properties. Drugs of this class suppress gastric acid secretion by the specific inhibition of the $H^+$, $K^+$-ATPase enzyme system (proton pump) at the secretory surface of the gastric parietal cell.

Typically, omeprazole, lansoprazole and other proton pump inhibitors are formulated in an enteric-coated solid dosage form (as either a delayed-release capsule or tablet) or as an intravenous solution (or as a product for reconstitution), and are prescribed for short-term treatment of active duodenal ulcers, gastric ulcers, gastroesophageal reflux disease (GERD), severe erosive esophagitis, poorly responsive systematic GERD, and pathological hypersecretory conditions such as Zollinger Ellison syndrome. These conditions are caused by an imbalance between acid and pepsin production, called aggressive factors, and mucous, bicarbonate, and prostaglandin production, called defensive factors. These above-listed conditions commonly arise in healthy or critically ill patients, and may be accompanied by significant upper gastrointestinal bleeding.

$H_2$-antagonists, antacids, and sucralfate are commonly administered to minimize the pain and the complications related to these conditions. These drugs have certain disadvantages associated with their use. Some of these drugs are not completely effective in the treatment of the aforementioned conditions and/or produce adverse side effects, such as mental confusion, constipation, diarrhea, and thrombocytopenia. $H_2$-antagonists, such as ranitidine and cimetidine, are relatively costly modes of therapy, particularly in NPO patients, which frequently require the use of automated infusion pumps for continuous intravenous infusion of the drug.

Patients with significant physiologic stress are at risk for stress-related gastric mucosal damage and subsequent upper gastrointestinal bleeding (Marrone and Silen, Pathogenesis, Diagnosis and Treatment of Acute Gastric Mucosa Lesions, Clin Gastroenterol 13: 635–650 (1984)). Risk factors that have been clearly associated with the development of stress-related mucosal damage are mechanical ventilation, coagulopathy, extensive burns, head injury, and organ transplant (Zinner et al., The Prevention of Gastrointestinal Tract Bleeding in Patients in an Intensive Care Unit, Surg. Gynecol. Obstet., 153: 214–220 (1981); Larson et al., Gastric Response to Severe Head Injury, Am. J. Surg. 147: 97–105 (1984); Czaja et al., Acute Gastroduodenal Disease After Thermal Injury: An Endoscopic Evaluation of Incidence and Natural History, N Engl. J. Med, 291: 925–929 (1974); Skillman et al., Respiratory Failure, Hypotension, Sepsis and Jaundice: A Clinical Syndrome Associated with Lethal Hemorrhage From Acute Stress Ulceration, Am. J. Surg., 117: 523–530 (1969); and Cook et al., Risk Factors for Gastrointestinal Bleeding in Critically Ill Patients, N. Engl. J. Med., 330:377–381 (1994)). One or more of these factors are often found in critically ill, intensive care unit patients. A recent cohort study challenges other risk factors previously identified such as acid-base disorders, multiple trauma, significant hypertension, major surgery, multiple operative procedures, acute renal failure, sepsis, and coma (Cook et al., Risk Factors for Gastrointestinal Bleeding in Critically Ill Patients, N. Engl. J. Med., 330:377–381 (1994)). Regardless of the risk type, stress-related mucosal damage results in significant morbidity and mortality. Clinically significant bleeding occurs in at least twenty percent of patients with one or more risk factors who are left untreated (Martin et al., Continuous Intravenous cimetidine Decreases Stress-related Upper Gastrointestinal Hemorrhage Without Promoting Pneumonia, Crit. Care Med., 21: 19–39 ('1993)). Of those who bleed, approximately ten percent require surgery (usually gastrectomy) with a reported mortality of thirty percent to fifty percent (Czaja et al., Acute Gastroduodenal Disease After Thermal Injury: An Endoscopic Evaluation of Incidence and Natural History, N Engl. J. Med, 291: 925–929 (1974); Peura and Johnson, Cimetidine for Prevention and Treatment of Gastroduodenal Mucosal Lesions in Patients in an Intensive Care Unit, Ann Intern Med., 103: 173–177 (1985)). Those who do not need surgery often require multiple transfusions and prolonged hospitalization. Prevention of stress-related upper gastrointestinal bleeding is an important clinical goal.

In addition to general supportive care, the use of drugs to prevent stress-related mucosal damage and related complications is considered by many to be the standard of care (AMA Drug Evaluations). However, general consensus is lacking about which drugs to use in this setting (Martin et al., Continuous Intravenous Cimetidine Decreases Stress-related Upper Gastrointestinal Hemorrhage Without Promoting Pneumonia, Crit. Care Med., 21: 19–39 (1993); Gafter et al., Thrombocytopenia Associated With Hypersensitivity to Ranitidine: Possible Cross-reactivity with Cimetidine, Am. J. Gastroenterol, 64: 560–562 (1989) Martin et al., Stress Ulcers and Organ Failure in Intubated Patients in Surgical Intensive Care Units, Ann Surg., 215: 332–337 (1992)). In two recent meta-analyses (Cook et al., Stress Ulcer Prophylaxis in the Critically Ill: A Meta-analysis, Am. J. Med., 91: 519–527 (1991); Tryba, Stress Ulcer Prophylaxis—Quo Vadis? Intens. Care Med. 20: 311–313 (1994)) Antacids, sucralfate, and $H_2$-antagonists were all found to be superior to placebo and similar to one another in preventing upper gastrointestinal bleeding. Yet, prophylactic agents are withdrawn in fifteen to twenty percent of patients in which they are employed because of failure to prevent bleeding or control pH (Ostro et al., Control of Gastric pH With Cimetidire Boluses Versus Primed Infusions, Gastroenterology, 89: 532–537 (1985) Siepler, A Dosage Alternative for H-2 Receptor Antagonists, Continuous-Infusion, Clin. Ther., 8 (Suppl A): 24–33 (1986); Ballesteros et al., Bolus or Intravenous Infusion of Ranitidine: Effects on Gastric pH and Acid Secretion: A Comparison of Relative Cost and Efficacy, Ann. Intern. Med., 112:334–339 (1990)), or because of adverse effects (Gafter et al., Thrombocytopenia Associated With Hypersensitivity to Ranitidine: Possible Cross-reactivity With Cimetidine, Am. J. Gastroenterol, 64: 560–562 (1989); Sax, Clinically Important Adverse Effects and Drug Interactions With H2-Receptor Antagonists: An Update, Pharmacotherapy 7(6 pt 2): 110S–115S (1987); Vial et al., Side Effects of Ranitidine, Drug Saf, 6:94–117(1991); Cantu and Korek, Central Nervous System Reactions to Histamine-2 Receptor Blockers, Ann. Intern Med., 114: 1027–1034 (1991); and Spychal and Wickham, Thrombocytopenia Associated With Ranitidine, Br. Med. J., 291: 1687 (1985)). In addition, the characteristics of an ideal agent for the prophylaxis of stress gastritis were analyzed by Smythe and Zarowitz, Changing Perspectives of Stress Gastritis Prophylaxis, Ann Pharmacother, 28: 1073–1084 (1994) who concluded that none of the agents-currently in use fulfill their criteria.

Stress ulcer prophylaxis has become routine therapy in intensive care units in most hospitals (Fabian et al., Pneumonia and Stress Ulceration in Severely Injured Patients, Arch. Surg., 128: 185–191 (1993); Cook et al., Stress Ulcer Prophylaxis in the Critically Ill: A Meta-Analysis, Am. J. Med., 91: 519–527 (1991)). Controversy remains regarding pharmacologic intervention to prevent stress-related bleeding in critical care patients. It has been suggested that the incidence and risk of gastrointestinal bleeding has decreased in the last ten years and drug therapy may no longer be needed (Cook et al., Risk Factors for Gastrointestinal Bleeding in Critically Ill. Patients, N. Engl. J. Med., 330:377–381 (1994); Tryba, Stress Ulcer Prophylaxis—Quo Vadis? Intens. Care Med. 20: 311–313 (1994); Schepp, Stress Ulcer Prophylaxis.: Still a Valid Option in the 1990s?, Digestion 54: 189–199 (1993)). This reasoning is not supported by a recent placebo-controlled study. Martin. et al. conducted a prospective, randomized, double-blind, placebo-controlled comparison of continuous-infusion cimetidine and placebo for the prophylaxis of stress-related mucosal damage. The study was terminated early because of excessive bleeding-related mortality in the placebo group. It appears that the natural course of stress-related mucosal damage in a patient at risk who receives no prophylaxis remains significant. In the placebo group, thirty-three percent (33%) of patients developed clinically significant bleeding, nine percent (9%) required transfusion, and six percent (6%) died due to bleeding-related complications. In comparison, fourteen percent (14%) of cimetidine-treated patients developed clinically significant bleeding, six percent (6%) required transfusions, and one and one-half percent (1.5%) died due to bleeding-related complication. The difference in bleeding rates between treatment groups was statistically significant. This study clearly demonstrated that continuous-infusion cimetidine reduced morbidity in critical care patients. Although these data were used to support the approval of continuous-infusion cimetidine by the Food and Drug Administration for stress ulcer prophylaxis, $H_2$-antagonists fall short of being the optimal pharmacotherapeutic agents for preventing of stress-related mucosal bleeding.

Another controversy surrounding stress ulcer prophylaxis is which drug to use. In addition to the various $H_2$-antagonists, antacids and sucralfate are other treatment options for the prophylaxis of stress-related mucosal damage. An ideal drug in this setting should possess the following characteristics: prevent stress ulcers and their complications, be devoid of toxicity, lack drug interactions, be selective, have minimal associated costs (such as personnel time and materials), and be easy to administer (Smythe and Zarowitz, Changing Perspectives of Stress Gastritis Prophylaxis, Ann Pharmacother, 28: 1073–1084 (1994)). Some have suggested that sucralfate is possibly the ideal agent for stress ulcer prophylaxis (Smythe and Zarowitz, Changing Perspectives of Stress Gastritis Prophylaxis, Ann Pharmacother, 28: 1073–1084 (1994)). Randomized, controlled studies support the use of sucralfate (Borrero et al., Antacids vs. Sucralfate in Preventing Acute Gastrointestinal Tract Bleeding in Abdominal Aortic Aurgery, Arch. Surg., 121: 810–812 (1986); Tryba, Risk of Acute Stress Bleeding and Nosocomial Pneumonia in Ventilated Intensive Care Patients. Sucralfate vs. Antacids, Am. J. Med., 87(3B): 117–124 (1987); Cioffi et al., Comparison of Acid Neutralizing and Non-acid Neutralizing Stress Ulcer Prophylaxis in Thermally Injured Patients. J. Trauma, 36: 541–547 (1994); and Driks et al., Nosocomial Pneumonia in Intubated Patients Given Sucralfate as Compared With Antacids or Histamine Type 2 Blockers, N. Engl. J. Med., 317: 1376–1382 1987)), but data on critical care patients with head injury, trauma, or burns are limited. In addition, a recent study comparing sucralfate and cimetidine plus antacids for stress ulcer prophylaxis reported clinically significant bleeding in three of forty-eight (6%) sucralfate-treated patients, one of whom required a gastrectomy (Cioffi et al., Comparison of Acid Neutralizing and Non-acid Neutralizing Stress Ulcer Prophylaxis in Thermally Injured Patients, J. Trauma, 36: 541–547 (1994)). In the study performed by Driks and coworkers that compared sucralfate to conventional therapy ($H_2$-antagonists, antacids, or $H_2$-antagonists plus antacids), the only patient whose death was attributed to stress-related upper gastrointestinal bleeding was in the sucralfate arm (Driks et al., Nosocomial Pneumonia in Intubated Patients Given Sucralfate as Compared With Antacids or Histamine Type 2 Blockers, N. Engl. J. Med., 317: 1376–1382(1987)).

$H_2$-antagonists fulfill many of the criteria for an ideal stress ulcer prophylaxis drug. Yet, clinically significant bleeds can occur during. $H_2$-antagonist prophylaxis (Martin et al., Continuous Intravenous Cimetidine Decreases Stress-related Upper Gastrointestinal Hemorrhage Without Promoting Pneumonia, Crit. Care Med., 21: 19–39 (1993); Cook et al. , Stress Ulcer Prophylaxis in the Critically Ill: A Meta-analysis, Am. J. Med., 91: 519–527 (1991); Schuman et al., Prophylactic Therapy for Acute Ulcer Bleeding: A Reappraisal, Ann Intern. Med, 106: 562–567 (1987)). Adverse events are not uncommon in the critical care population (Gafter et al., Thrombocytopenia Associated With Hypersensitivity to Ranitidine: Possible Cross-Reactivity With Cimetidine, Am. J. Gastroenterol, 64: 560–562 (1989); Sax, Clinically Important Adverse Effects and Drug Interactions With H2-receptor Antagonists: An Update, Pharmacotherapy 7(6 pt 2): 110S–115S (1987); Vial et al., Side Effects of Ranitidine, Drug Saf., 6:94–117(1991); Cantu and Korek, Central Nervous System Reactions to Histamine-2 Receptor Blockers, Ann. Intern Med., 114: 1027–1034 (1991); Spychal and Wickham, Thrombocytopenia Associated With Ranitidine, Br. Med. J., 291: 1687 (1985)).

One reason proposed for the therapeutic $H_2$-antagonist failures is lack of pH control throughout the treatment period (Ostro et al., Control of Gastric pH With Cimetidine Boluses Versus Primed Infusions, Gastroenterology, 89: 532–537 (1985)). Although the precise pathophysiologic mechanisms involved in stress ulceration are not clearly established, the high concentration of hydrogen ions in the mucosa (Fiddian-Green et al., 1987) or gastric fluid in contact with mucosal cells appears to be an important factor. A gastric pH >3.5 has been associated with a lower incidence of stress-related mucosal damage and bleeding (Larson et al., Gastric Response to Severe Head Injury, Am. J. Surg. 147: 97–105 (1984); Skillman et al., Respiratory Failure, Hypotension, Sepsis and Jaundice: A Clinical Syndrome Associated With Lethal Hemorrhage From Acute Stress Ulceration, Am. J. Surg., 117: 523–530 (1969); Skillman et al., The Gastric Mucosal Barrier: Clinical and Experimental Studies in Critically Ill and Normal Man and in the Rabbit, Ann Surg., 172: 564–584 (1970); and Priebe and Skillman, Methods of Prophylaxis in Stress Ulcer Disease, World J. Surg., 5: 223–233 (1981)). Several studies have shown that $H_2$-antagonists, even in maximal doses, do not reliably or continuously increase intragastric pH above commonly targeted levels (3.5 to 4.5). This is true especially when used in fixed-dose bolus regimens (Ostro et al., Control of Gastric pH With Cimetidine Boluses Versus Primed Infusions, Gastroenterology, 89: 532–537 (1985); Siepler, A Dosage Alternative for H-2 Receptor Antagonists, Continuous-infusion, Clin. Ther., 8 (Suppl A): 24–33 (1986); Ballesteros et al., Bolus or Intravenous Infusion of Ranitidine: Effects on Gastric pH and Acid Secretion: A Comparison of Relative Cost and Efficacy, Ann. Intern. Med., 112:334–339 (1990)). In addition, gastric pH levels tend to trend downward with time when using a continuous-infusion of $H_2$-antagonists, which may be the result of tachyphylaxis (Ostro et al., Control of Gastric pH With Cimetidine Boluses Versus Primed Infusions, Gastroenterology, 89: 532–537 (1985); Wilder-Smith and Merki, Tolerance During Dosing With $H_2$-receptor Antagonists. An Overview, Scand. J. Gastroenterol 27 (suppl. 193): 14–19 (1992)).

Because stress ulcer prophylaxis is frequently employed in the intensive care unit, it is essential from both a clinical and economic standpoint to optimize the pharmacotherapeutic approach. In an attempt to identify optimal therapy, cost of care becomes an issue. All treatment costs should be considered, including the costs of treatment failures and drug-related adverse events. While the actual number of failures resulting in mortality is low, morbidity (e.g., bleeding that requires blood transfusion) can be high, even though its association with the failure of a specific drug is often unrecognized.

Initial reports of increased frequency of pneumonia in patients receiving stress ulcer prophylaxis with agents that raise gastric pH has influenced the pharmacotherapeutic approach to management of critical care patients. However, several recent studies (Simms et al., Role of Gastric Colonization in the Development of Pneumonia in Critically Ill Trauma Patients: Results of a Prospective Randomized Trial, J. Trauma, 31: 531–536 (1991); Pickworth et al., Occurrence of Nasocomial Pneumonia in Mechanically Ventilated Trauma Patients: A Comparison of Sucralfate and Ranitidine, Crit. Care Med., 12: 1856–1862 (1993); Ryan et al., Nasocomial Pneumonia During Stress Ulcer Prophylaxis With Cimetidine and Sucralfate, Arch. Surg., 128: 1353–1357 (1993); Fabian et al., Pneumonia and Stress Ulceration in Severely Injured Patients, Arch. Surg., 128: 185–191 (1993)), a meta-analysis (Cook et al., Stress Ulcer Prophylaxis in the Critically Ill: A Meta-analysis, Am. J. Med., 91: 519–527 (1991)), and a closer examination of the studies that initiated the elevated pH-associated pneumonia hypotheses (Schepp, Stress Ulcer Prophylaxis: Still a Valid Option in the 1990s?, Digestion 54: 189–199 (1993)) cast doubt on a causal relationship. The relationship between pneumonia and antacid therapy is much stronger than for $H_2$-antagonists. The shared effect of antacids and $H_2$-antagonists on gastric pH seems an irresistible common cause explanation for nosocomial pneumonia observed during stress ulcer prophylaxis. However, there are important differences between these agents that are not often emphasized (Laggner et al., Prevention of Upper Gastrointestinal Bleeding in Long-term Ventilated Patients, Am. J. Med., 86 (suppl 6A) : 81–84 (1989)). When antacids are exclusively used to control pH in the prophylaxis of stress-related upper gastrointestinal bleeding, large volumes are needed. Volume, with or without subsequent reflux, may be the underlying mechanism(s) promoting the development of pneumonia in susceptible patient populations rather than the increased gastric pH. The rate of pneumonia (12%) was not unexpected in this critical care population and compares with sucralfate, which does not significantly raise gastric pH (Pickworth et al., Occurrence of Nasocomial Pneumonia in Mechanically Ventilated Trauma Patients: A Comparison of Sucralfate and Ranitidine, Crit. Care Med., 12: 1856–1862 (1993); Ryan et al., Nasocomial Pneumonia During Stress Ulcer Prophylaxis With Cimetidine and Sucralfate, Arch. Surg., 128: 1353–1357 (1993)).

Omeprazole (Prilosec®), lansoprazole (Prevacid®) and other PPIs reduce gastric acid production by inhibiting $H^+,K^+$-ATPase of the parietal cell-the final common pathway for gastric acid secretion (Fellenius et al., Substituted Benzimidazoles Inhibit Gastric Acid Secretion by Blocking $H^+,K^+$-ATPase, Nature, 290: 159–161 (1981); Wallmark et al, The Relationship Between Gastric Acid Secretion and Gastric $H^+,K^+$-ATPase Activity, J. Biol. Chem., 260: 13681–13684 (1985); Fryklund et al., Function and Structure of Parietal Cells After $H^+,K^+$-ATPase Blockade, Am. J. Physiol., 254 (3 pt 1) ; G399–407 (1988)).

PPIs contain a sulfinyl group in a bridge between substituted benzimidazole and pyridine rings, as illustrated below.

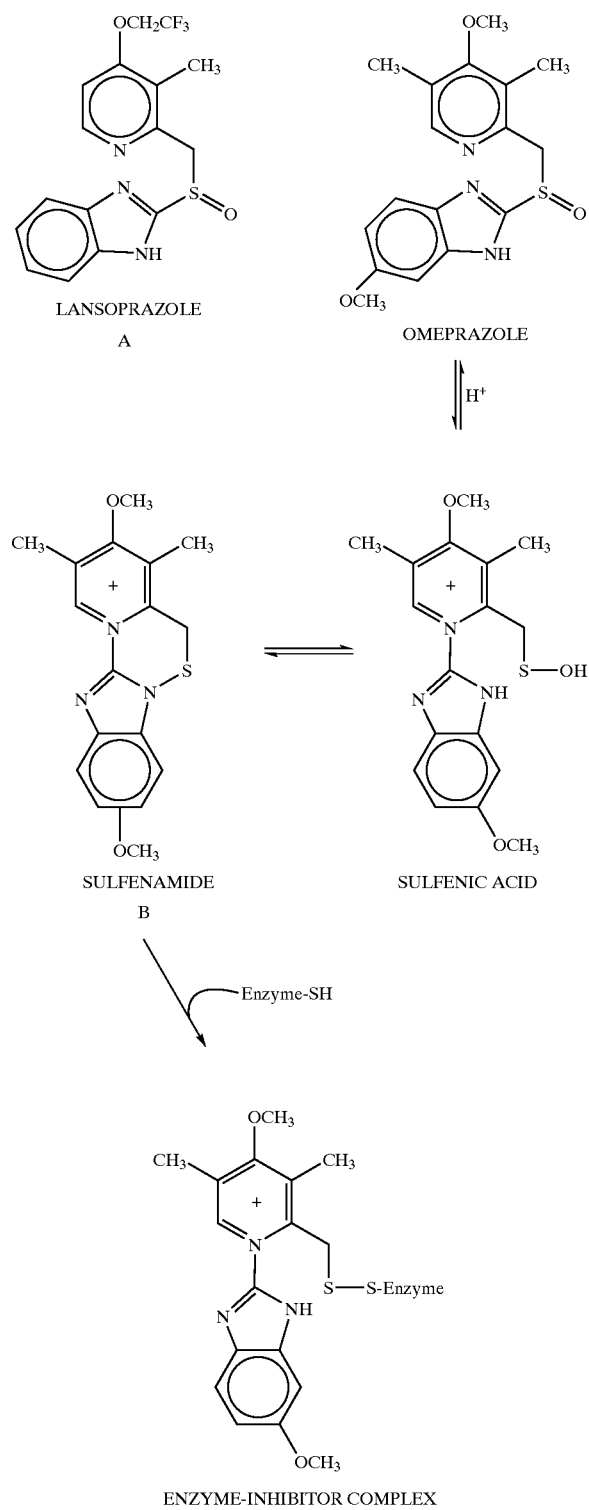

At neutral pH, omeprazole, lansoprazole and other PPIs are chemically stable, lipid-soluble, weak bases that are devoid of inhibitory activity. These neutral weak bases reach parietal cells from the blood and diffuse into the secretory canaliculi, where the drugs become protonated and thereby trapped. The protonated agent rearranges to form a sulfenic acid and a sulfenamide. The sulfenamide interacts covalently with sulfhydryl groups at critical sites in the extracellular (luminal) domain of the membrane-spanning $H^+,K^+$-ATPase (Hardman et al., *Goodman & Gilman's The Pharmacological Basis of Therapeutics,* p. 907 ($9^{th}$ ed. 1996)). Omeprazole and lansoprazole, therefore, are pro-drugs that must be activated to be effective. The specificity of the effects of PPIs is also dependent upon: (a) the selective distribution of $H^+,K^+$-ATPase; (b) the requirement for acidic conditions to catalyze generation of the reactive inhibitor; and (c) the trapping of the protonated drug and the cationic sulfenamide within the acidic canaliculi and adjacent to the target enzyme. (Hardman et al., 1996)).

Omeprazole and lansoprazole are available for oral administration as enteric coated particles in gelatin capsules. Other proton pump inhibitors such as rabeprazole and pantoprazole are supplied as enteric coated tablets. The enteric dosage forms of the prior art have been employed because it is very important that these drugs not be exposed to gastric acid prior to absorption. Although these drugs are stable at alkaline pH, they are destroyed rapidly as pH falls (e.g., by gastric acid). Therefore, if the microencapsulation or the enteric coating is disrupted (e.g., trituration to compound a liquid, or chewing the capsule), the drug will be exposed to degradation by the gastric acid in the stomach.

The absence of an intravenous or oral liquid dosage form in the United-States has limited the testing and use of omeprazole, lansoprazole and rabeprazole in the critical care patient population. Barie et al., Therapeutic Use of Omeprazole for Refractory Stress-induced Gastric Mucosal Hemorrhage, Crit. Care Med., 20: 899–901 (1992) have described the use of omeprazole enteric-coated pellets administered through a nasogastric tube to control gastrointestinal hemorrhage in a critical care patient with multi-organ failure. However, such pellets are not ideal as they can aggregate and occlude such tubes, and they are not suitable for patients who cannot swallow the pellets. Am J. Health-Syst Pharm 56:2327–30 (1999).

Proton pump inhibitors such as omeprazole represent an advantageous alternative to the use of $H_2$-antagonists, antacids, and sucralfate as a treatment for complications related to stress-related mucosal damage. However, in their current form (capsules containing enteric-coated granules or enteric-coated tablets), proton pump inhibitors can be difficult or impossible to administer to patients who are either-unwilling or unable to swallow tablets or capsules, such as critically ill patients, children, the elderly, and patients suffering from dysphagia. Therefore, it would be desirable to formulate a proton pump inhibitor solution or suspension which can be enterally delivered to a patient thereby providing the benefits of the proton pump inhibitor without the drawbacks of the current enteric-coated solid dosage forms.

Omeprazole, the first proton pump inhibitor introduced into use, has been formulated in many different embodiments such as in a mixture of polyethylene glycols, adeps solidus and sodium lauryl sulfate in a soluble, basic amino acid to yield a formulation designed for administration in the rectum as taught by U.S. Pat. No. 5,219,870 to Kim.

U.S. Pat. No. 5,395,323 to Berglund ('323) discloses a device for mixing a pharmaceutical from a solid supply into a parenterally acceptable liquid form for parenteral administration to a patient. The '323 patent teaches the use of an omeprazole tablet which is placed in the device and dissolved by normal saline, and infused parenterally into the patient. This device and method of parenteral infusion of omeprazole does not provide the omeprazole solution as an enteral product, nor is this omeprazole solution directly administered to the diseased or affected areas, namely the stomach and upper gastrointestinal tract, nor does this omeprazole formulation provide the immediate antacid effect of the present formulation..

U.S. Pat. No. 4,786,505 to Lovgren et al. discloses a pharmaceutical preparation containing omeprazole together with an alkaline reacting compound or an alkaline salt of omeprazole optionally together with an alkaline compound as a core material in a tablet formulation. The use of the alkaline material, which can be chosen from such substances as the sodium salt of carbonic acid, are used to form a "micro-pH" around each omeprazole particle to protect the omeprazole which is highly sensitive to acid pH. The powder mixture is then formulated to small beads, pellets, tablets and may be loaded into capsules by conventional pharmaceutical procedures. This formulation of omeprazole does not provide an omeprazole dosage form which can be enterally administered to a patient who may be unable and/or unwilling to swallow capsules, tablets or pellets, nor does it teach a convenient form which can be used to make an omeprazole or other proton pump inhibitor solution or suspension.

Several buffered omeprazole oral solutions/suspensions have been disclosed. For example, Pilbrant et al., Development of an Oral Formulation of Omeprazole, Scand. J. Gastroent. 20 (Suppl. 108): 113–120 (1985) teaches the use of micronized omeprazole suspended in water, methylcellulose and sodium bicarbonate in a concentration of approximately 1.2 mg omeprazole/ml suspension.

Andersson et el., Pharmacokinetics of Various Single Intravenous and Oral Doses of Omeprazole, Eur J. Clin. Pharmacol. 39:, 195–197 (1990) discloses 10 mg, 40 mg, and 90 mg of oral omeprazole dissolved in PEG 400, sodium bicarbonate and water. The concentration of omeprazole cannot be determined as volumes of diluent are not disclosed. Nevertheless, it is apparent from this reference that multiple doses of sodium bicarbonate were administered with and after the omeprazole suspension.

Andersson et al., Pharmacokinetics and Bioavailability of Omeprazole After Single and Repeated Oral Administration in Healthy Subjects, Br. J. Clin. Pharmac. 29: 557–63 (1990) teaches the oral use of 20 mg of omeprazole, which was dissolved in 20 g of PEG 400 (sp. gravity=1.14) and diluted with 50 ml of sodium bicarbonate, resulting in a concentration of 0.3 mg/ml.

Regardh et al., The Pharmacokinetics of Omeprazole in Humans—A Study of Single Intravenous and Oral Doses, Ther. Drug Mon. 12: 163–72 (1990) discloses an oral dose of omeprazole at a concentration 0.4 mg/ml after the drug was dissolved in PEG 400, water and sodium bicarbonate.

Landahl et al., Pharmacokinetics Study of Omeprazole in Elderly Healthy Volunteers, Clin. Pharmacokinetics 23 (6): 469–476 (1992) teaches the use of an oral dose of 40 mg of omeprazole dissolved in PEG 400, sodium bicarbonate and water. This reference does not disclose the final concentrations utilized. Again, this reference teaches the multiple administration of sodium bicarbonate after the omeprazole solution.

Andersson et al., Pharmacokinetics of [$^{14}$C] Omeprazole in Patients with Liver Cirrhosis, Clin. Pharmacokinetics 24(1): 71–78 (1993) discloses the oral administration of 40 mg of omeprazole which was dissolved in PEG 400, water and sodium bicarbonate. This reference does not teach the final concentration of the omeprazole solution administered, although it emphasizes the need for concomitant sodium bicarbonate dosing to prevent acid degradation of the drug.

Nakagawa, et al., Lansoprazole: Phase I Study of lansoprazole (AG-1749) Anti-ulcer Agent, J. Clin. Therapeutics & Med. (1991) teaches the oral administration of 30 mg of lansoprazole suspended in 100 ml of sodium bicarbonate (0.3 mg/ml), which was administered to patients through a nasogastric tube.

All of the buffered omeprazole solutions described in these references were administered orally, and were given to healthy subjects who were able to ingest the oral dose. In all of these studies, omeprazole was suspended in a solution including sodium bicarbonate, as a pH buffer, in order to protect the acid sensitive omeprazole during administration. In all of these studies, repeated administration of sodium bicarbonate both prior to, during, and following omeprazole administration were required in order to prevent acid degradation of the omeprazole given via the oral route of administration. In the above-cited studies, as much as 48 mmoles of sodium bicarbonate in 300 ml of water must be ingested for a single dose of omeprazole to be orally administered.

The buffered omeprazole solutions of the above cited prior art require the ingestion of large amounts of sodium bicarbonate and large volumes of water by repeated administration. This has been considered necessary to prevent acid degradation of the omeprazole. In the above-cited studies, basically healthy volunteers, rather than sick patients, were given dilute buffered omeprazole utilizing pre-dosing and post-dosing with large volumes of sodium bicarbonate.

The administration of large amounts of sodium bicarbonate can produce at least six significant adverse effects, which can dramatically reduce the efficacy of the omeprazole in patients and reduce the overall health of the patients. First, the fluid volumes of these dosing protocols would not be suitable for sick or critically ill patients who must receive multiple doses of omeprazole. The large volumes would result in the distention of the stomach and increase the likelihood of complications in critically ill patients such as the aspiration of gastric contents.

Second, because bicarbonate is usually neutralized in the stomach or is absorbed, such that belching results, patients with gastroesophageal reflux may exacerbate or worsen their reflux disease as the belching can cause upward movement of stomach acid (Brunton, Agents for the Control of Gastric Acidity and Treatment of Peptic Ulcers, In, Goodman A G, et al. The Pharmacologic Basis of Therapeutics (New York, p. 907 (1990)).

Third, patients with conditions such as hypertension or heart failure are standardly advised to avoid the intake of excessive sodium as it can cause aggravation or exacerbation of their hypertensive conditions (Brunton, supra). The ingestion of large amounts of sodium bicarbonate is inconsistent with this advice.

Fourth, patients with numerous conditions that typically accompany critical illness should avoid the intake of excessive sodium bicarbonate as it can cause metabolic alkalosis that can result in a serious worsening of the patient's condition.

Fifth, excessive antacid intake (such as sodium bicarbonate) can result in drug interactions that produce serious adverse effects. For example, by altering gastric and urinary pH, antacids can alter rates of drug dissolution and absorption, bioavailability, and renal elimination (Brunton, supra).

Sixth, because the buffered omeprazole solutions of the prior art require prolonged administration of sodium bicarbonate, it makes it difficult for patients to comply with the regimens of the prior art. For example, Pilbrant. et al. disclose an oral omeprazole administration protocol calling for the administration to a subject who has been fasting for at least ten hours, a solution of 8 mmoles of sodium bicarbonate in 50 ml of water. Five minutes later, the subject ingests a suspension of 60 mg of omeprazole in 50 ml of water that also contains 8 mmoles of sodium bicarbonate. This is rinsed down with another 50 ml of 8 mmoles sodium bicarbonate solution. Ten minutes after the ingestion of the omeprazole dose, the subject ingests 50 ml of bicarbonate solution (8 mmoles). This is repeated at twenty minutes and thirty minutes post omeprazole dosing to yield a total of 48 mmoles of, sodium bicarbonate and 300 ml of water in total which are ingested by the subject for a single omeprazole dose. Not only does this regimen require the ingestion of excessive amounts of bicarbonate and water, which is likely to be dangerous to some patients, it is unlikely that even healthy patients would comply with this regimen.

It is well documented that patients who are required to follow complex schedules for drug administration are non-compliant and, thus, the efficacy of the buffered omeprazole solutions of the prior art would be expected to be reduced due to non-compliance. Compliance has been found to be markedly reduced when patients are required to deviate from a schedule of one or two (usually morning and night) doses of a medication per day. The use of the prior art buffered omeprazole solutions which require administration protocols with numerous steps, different drugs (sodium bicarbonate+omeprazole+PEG 400 versus sodium bicarbonate alone), and specific time allotments between each stage of the total omeprazole regimen in order to achieve efficacious results is clearly in contrast with both current drug compliance theories and human nature.

The prior art (Pilbrant et al., 1985) teaches that the buffered omeprazole suspension can be stored at refrigerator temperatures for a week and deep frozen for a year while still maintaining 99% of its initial potency. It would be desirable to have an omeprazole or other proton pump inhibitor solution or suspension that could be stored at room temperature or in a refrigerator, for periods of time which exceed those of the prior art while still maintaining 99% of the initial potency. Additionally, it would be advantageous to have a form of the omeprazole and bicarbonate which can be utilized to instantly make the omeprazole solution/suspension of the present invention which is supplied in a solid form which imparts the advantages of improved shelf-life at room temperature, lower cost to produce, less expensive shipping costs, and which is less expensive to store.

It would, therefore, be desirable to have a proton pump inhibitor formulation, which provides a cost-effective means for the treatment of the aforementioned conditions without the adverse effect profile of $H_2$ receptor antagonists, antacids, and sucralfate. Further, it would be desirable to have a proton pump inhibitor formulation which is convenient to prepare and administer to patients unable to ingest solid dosage forms such as tablets or capsules, which is rapidly absorbed, and can be orally or enterally delivered as a liquid form or solid form. It is desirable that the liquid formulation not clog indwelling tubes, such as nasogastric tubes or other similar tubes, and which acts as an antacid immediately upon delivery.

It would further be advantageous to have a potentiator or enhancer of the pharmacological activity of the PPIs. It has been theorized by applicant that the PPIs can only exert their effects on $H^+,K^+$-ATPase when the parietal cells are active. Accordingly, applicant has identified, as discussed below, parietal cell activators that are administered to synergistically enhance the activity of the PPIs.

Additionally, the intravenous dosage forms of PPIs of the prior art are often administered in larger doses than the oral forms. For example, the typical adult IV dose of omeprazole is greater than 100 mg/day whereas the adult oral dose is 20 to 40 mg/day. Large IV doses are necessary to achieve the desired pharmacologic effect because, it is believed, many of the parietal cells are in a resting phase (mostly inactive) during an IV dose given to patients who are not taking oral substances by mouth (npo) and, therefore, there is little active (that which is inserted into the secretory canalicular membrane) $H^+,K^+$-ATPase to inhibit. Because of the clear disparity in the amount of drug necessary for IV versus oral doses, it would be very advantageous to have compositions and methods for IV administration where significantly less drug is required.

SUMMARY OF THE INVENTION AND ADVANTAGES

The foregoing advantages and objects are accomplished by the present invention. The present invention provides an oral solution/suspension comprising a proton pump inhibitor and at least one buffering agent. The PPI can be any substituted benzimidazole compound having $H^+,K^+$-ATPase inhibiting activity and being unstable to acid. Omeprazole and lansoprazole are the preferred PPIs for use in oral suspensions in concentrations of at least 1.2 mg/ml and 0.3 mg/ml, respectively. The liquid oral compositions can be further comprised of parietal cell activators, anti-foaming agents and/or flavoring agents.

The inventive composition can alternatively be formulated as a powder, tablet, suspension tablet, chewable tablet, capsule, effervescent powder, effervescent tablet, pellets and granules. Such dosage forms are advantageously devoid of any enteric coating or delayed or sustained-release delivery mechanisms, and comprise a PPI and at least one buffering agent to protect the PPI against acid degradation. Similar to the liquid dosage form, the dry forms can further include anti-foaming agents, parietal cell activators and flavoring agents.

Kits utilizing the inventive dry dosage forms are also disclosed herein to provide for the easy preparation of a liquid composition from the dry forms.

In accordance with the present invention, there is further provided a method of treating gastric acid disorders by administering to a patient a pharmaceutical composition comprising a proton pump inhibitor in a pharmaceutically acceptable carrier and at least one buffering agent wherein the administering step comprises providing a patient with a single dose of the composition without requiring further administering of the buffering agent.

Additionally, the present invention relates to a method for enhancing the pharmacological activity of an intravenously administered proton pump inhibitor in which at least one parietal cell activator is orally administered to the patient before, during and/or after the intravenous administrations of the proton pump inhibitor.

BRIEF DESCRIPTION OF THE DRAWINGS

Other advantages of the present invention will be readily appreciated as the same becomes better understood by reference to the following detailed description when considered in connection with the accompanying drawing wherein.

DETAILED DESCRIPTION OF THE INVENTION

Figure 1:
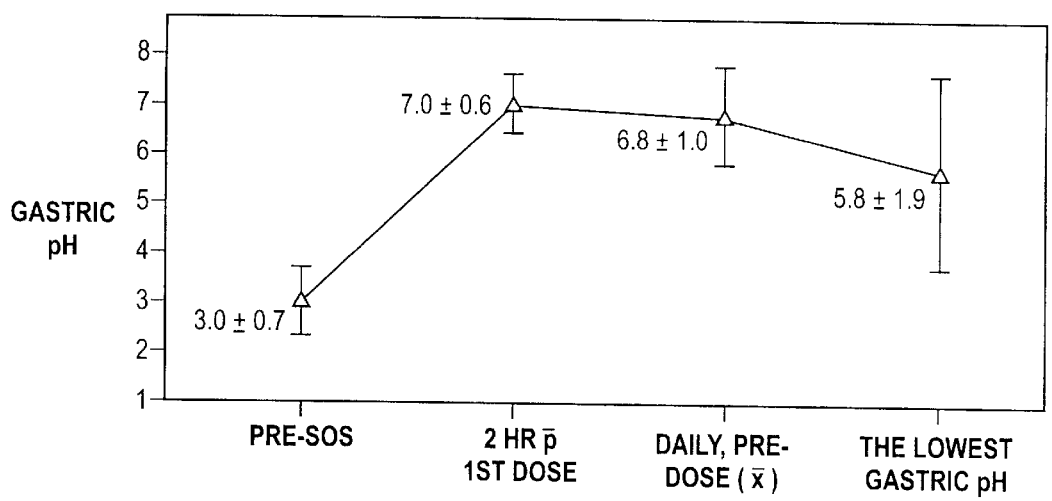
FIG. 1 is a graph showing the effect of the omeprazole solution of the present invention on gastric pH in patients at risk for upper gastrointestinal bleeding from stress-related mucosal damage.

In general, the present invention relates to a pharmaceutical composition comprising a proton pump inhibitor and a buffering agent with or without one or more parietal cell activators. While the present invention may be embodied in many different forms, several specific embodiments are discussed herein with the understanding that the present disclosure is to be considered only as an exemplification of the principles of the invention, and it is not intended to limit the invention to the embodiments illustrated.

For the purposes of this application, the term "proton pump inhibitor" (PPI) shall mean any substituted benzimidazole possessing pharmacological activity as an inhibitor of $H^+,K^+$-ATPase, including, but not limited to, omeprazole, lansoprazole, pantoprazole, rabeprazole, dontoprazole, perprazole (s-omeprazole magnesium), habeprazole, ransoprazole, pariprazole, and leminoprazole in neutral form or a salt form, a single enantiomer or isomer or other derivative or an alkaline salt of an enantiomer of the same.

The inventive composition comprises dry formulations, solutions and/or suspensions of the proton pump inhibitors. As used herein, the terms "suspension" and "solution" are interchangeable with each other and mean solutions and/or suspensions of the substituted benzimidazoles.

After absorption of the PPI (or administration intravenously) the drug is delivered via the bloodstream to various tissues and cells of the body including the parietal cells. Research suggests that the PPI is in the form of a weak base and is non-ionized and thereby freely passes through physiologic membranes, including the cellular membranes of the parietal cell. It is believed that the non-ionized PPI moves into the acid-secreting portion of the parietal cell, the secretory canaliculus. Once in the acidic millieu of the secretory canaliculus, the PPI is apparently protonated (ionized) and converted to the active form of the drug. Generally, ionized proton pump inhibitors are membrane impermeable and form disulfide covalent bonds with cysteine residues in the alpha subunit of the proton pump.

The inventive pharmaceutical composition comprising a proton pump inhibitor such as omeprazole, lansoprazole or other proton pump inhibitor and derivatives thereof can be used for the treatment or prevention of gastrointestinal conditions including, but not limited to, active duodenal ulcers, gastric ulcers, gastroesophageal reflux disease (GERD), severe erosive esophagitis, poorly responsive systematic GERD, and pathological hypersecretory conditions such as Zollinger Ellison Syndrome. Treatment of these conditions is accomplished by administering to a patient an effective amount of the pharmaceutical composition according to the present invention.

The proton pump inhibitor is administered and dosed in accordance with good medical practice, taking into account the clinical condition of the individual patient, the site and method of administration, scheduling of administration, and other factors known to medical practitioners. The term "effective amount" means, consistent with considerations known in the art, the amount of PPI or other agent effective to achieve a pharmacologic effect or therapeutic improvement without undue adverse side effects, including but not limited to, raising of gastric pH, reduced gastrointestinal bleeding, reduction in the need for blood transfusion, improved survival rate, more rapid recovery, parietal cell activation and $H^+,K^+$-ATPase inhibition or improvement or elimination of symptoms, and other indicators as are selected as appropriate measures by those skilled in the art.

The dosage range of omeprazole or other proton pump inhibitors such as substituted benzimidazoles and derivatives thereof can range from approximately <2 mg/day to approximately 300 mg/day. The standard approximate daily oral dosage is typically 20 mg of omeprazole, 30 mg lansoprazole, 40 mg pantoprazole, 20 mg rabeprazole, and the pharmacologically equivalent doses of the following PPIs: habeprazole, pariprazole, dontoprazole, ransoprazole, perprazole (s-omeprazole magnesium), and leminoprazole.

A pharmaceutical formulation of the proton pump inhibitors utilized in the present invention can be administered orally or enterally to the patient. This can be accomplished, for example, by administering the solution via a nasogastric (ng) tube or other indwelling tubes placed in the GI tract. In order to avoid the critical disadvantages associated with administering large amounts of sodium bicarbonate, the PPI solution of the present invention is administered in a single dose which does not require any further administration of bicarbonate, or large amounts of bicarbonate, or other buffer following the administration of the PPI solution, nor does it require a large amount of bicarbonate or buffer in total. That is, unlike the prior art PPI solutions and administration protocols outlined above, the formulation of the present invention is given in a single dose which does not require administration of bicarbonate either before or after administration of the PPI. The present invention eliminates the need to pre-or post-dose with additional volumes of water and sodium bicarbonate. The amount of bicarbonate administered via the single dose administration of the present invention is less than the amount of bicarbonate administered as taught in the prior art references cited above.

Preparation of Oral Liquids

The liquid oral pharmaceutical composition of the present invention is prepared by mixing omeprazole (Prilosec® AstraZeneca) or other proton pump inhibitor or derivatives thereof with a solution including at least one buffering agent (with or without a parietal cell activator, as discussed below). Preferably, omeprazole or other proton pump inhibitor, which can be obtained from a capsule or tablet or obtained from the solution for parenteral administration, is mixed with a sodium bicarbonate solution to achieve a desired final omeprazole (or other PPI) concentration. As an example, the concentration of omeprazole in the solution can range from approximately 0.4 mg/ml to approximately 10.0 mg/ml. The preferred concentration for the omeprazole in the solution ranges from approximately 1.0 mg/ml to approximately 4.0 mg/ml, with 2.0 mg/ml being the standard concentration. For lansoprazole (Prevacid® TAP Pharmaceuticals, Inc.) the concentration can range from about 0.3 mg/ml to 10 mg/ml with the preferred concentration being about 3 mg/ml.

Although sodium bicarbonate is the preferred buffering agent employed in the present invention to protect the PPI against acid degradation, many other weak and strong bases (and mixtures thereof) can be utilized. For the purposes of this application, "buffering agent" shall mean any pharmaceutically appropriate weak base or strong base (and mixtures thereof) that, when formulated or delivered with (e.g., before, during and/or after) the PPI, functions to substantially prevent or inhibit the acid degradation of the PPI by gastric acid sufficient to preserve the bioavailability of the PPI administered. The buffering agent is administered in an amount sufficient to substantially achieve the above functionality. Therefore, the buffering agent of the present invention, when in the presence of gastric acid, must only elevate the pH of the stomach sufficiently to achieve adequate bioavailability of the drug to effect therapeutic action.

Accordingly, examples of buffering agents include, but are not limited to, sodium bicarbonate, potassium bicarbonate, magnesium hydroxide, magnesium lactate, magnesium glucomate, aluminum hydroxide, aluminum hydroxide/sodium bicarbonate coprecipitate, a mixture of an amino acid and a buffer, a mixture of aluminum glycinate and a buffer, a mixture of an acid salt of an amino acid and a buffer, and a mixture of an alkali salt of an amino acid and a buffer. Additional buffering agents include sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium cholride, calcium hydroxide, calcium lactate, calcium carbonate, calcium bicarbonate, and other calcium salts.

The pharmaceutically acceptable carrier of the oral liquid preferably comprises a bicarbonate salt of Group IA metal as buffering agent, and can be prepared by mixing the bicarbonate salt of the Group IA metal, preferably sodium bicarbonate, with water. The concentration of the bicarbonate salt of the Group IA metal in the composition generally ranges from approximately 5.0 percent to approximately 60.0 percent. Preferably, the concentration of the bicarbonate salt of the Group IA metal ranges from approximately 7.5 percent to approximately 10.0 percent. In a preferred embodiment of the present invention, sodium bicarbonate is the preferred salt and is present in a concentration of approximately 8.4 percent.

More specifically, the amount of sodium bicarbonate 8.4% used in the solution of the present invention is approximately 1 mEq (or mmole) sodium bicarbonate per 2 mg omeprazole, with a range of approximately 0.2 mEq (mmole) to 5 mEq (mmole) per 2 mg of omeprazole.

In a preferred embodiment of the present invention, enterically-coated omeprazole particles are obtained from delayed release capsules (Prilosec® AstraZeneca). Alternatively, omeprazole powder can be used. The enterically coated omeprazole particles are mixed with a sodium bicarbonate ($NaHCO_3$) solution (8.4%), which dissolves the enteric coating and forms an omeprazole solution. The omeprazole solution has pharmacokinetic advantages over standard time-released omeprazole capsules, including: (a) more rapid drug absorbance time (about 10 to 60 minutes) following administration for the omeprazole solution versus about 1 to 3 hours following administration for the enteric-coated pellets; (b) the $NaHCO_3$ solution protects the omeprazole from acid degradation prior to absorption; (c) the $NaHCO_3$ acts as an antacid while the omeprazole is being absorbed; and (d) the solution can be administered through an existing indwelling tube without clogging, for example, nasogastric or other feeding tubes (jejunal or duodenal), including small bore needle catheter feeding tubes.

Additionally, various additives can be incorporated into the inventive solution to enhance its stability, sterility and isotonicity. Further, antimicrobial preservatives, antioxidants, chelating agents, and additional buffers can be added, such as ambicin. However, microbiological evidence shows that this formulation inherently possesses antimicrobial and antifungal activity. Various antibacterial and antifungal agents such as, for example, parabens, chlorobutanol, phenol, sorbic acid, and the like can enhance prevention of the action of microorganisms.

In many cases, it would be desirable to include isotonic agents, for example, sugars, sodium chloride, and the like. Additionally, thickening agents such as methylcellulose are desirable to use in order to reduce the settling of the omeprazole or other PPI or derivatives thereof from the suspension.

The liquid oral solution may further comprise flavoring agents (e.g., chocolate, root beer or watermelon) or other flavorings stable at pH 7 to 9, anti-foaming agents (e.g., simethicone 80 mg, Mylicon®) and parietal cell activators (discussed below).

The present invention further includes a pharmaceutical composition comprising omeprazole or other proton pump inhibitor and derivatives thereof and at least one buffering agent in a form convenient for storage, whereby when the composition is placed into an aqueous solution, the composition dissolves yielding a suspension suitable for enteral administration to a subject. The pharmaceutical composition is in a solid form prior to dissolution or suspension in an aqueous solution. The omeprazole or other PPIs and buffering agent can be formed into a tablet, capsule, pellets or granules, by methods well known to those skilled in the art.

The resultant omeprazole solution is stable at room temperature for several weeks and inhibits the growth of bacteria or fungi as shown in Example X below. Indeed, as established in Example XIII, the solution maintains greater than 90% of its potency for 12 months. By providing a pharmaceutical composition including omeprazole or other PPI with buffer in a solid form, which can be later dissolved or suspended in a prescribed amount of aqueous solution to yield the desired concentration of omeprazole and buffer, the cost of production, shipping, and storage are greatly reduced as no liquids are shipped (reducing weight and cost), and there is no need to refrigerate the solid form of the composition or the solution. Once mixed the resultant solution can then be used to provide dosages for a single patient over a course of time, or for several patients.

Tablets and Other Solid Dosage Forms

As mentioned above, the formulations of the present invention can also be manufactured in concentrated forms, such as tablets, suspension tablets and effervescent tablets or powders, such that upon reaction with water or other diluent, the aqueous form of the present invention is produced for oral, enteral or parenteral administration.

The present pharmaceutical tablets or other solid dosage forms disintegrate rapidly in aqueous media and form an aqueous solution of the PPI and buffering agent with minimal shaking or agitation. Such tablets utilize commonly available materials and achieve these and other desirable objectives. The tablets or other solid dosage forms of this invention provide for precise dosing of a PPI that may be of low solubility in water. They are particularly useful for medicating children and the elderly and others in a way that is much more acceptable than swallowing or chewing a tablet. The tablets that are produced have low friability, making them easily transportable.

The term "suspension tablets" as used herein refers to compressed tablets which rapidly disintegrate after they are placed in water, and are readily dispersible to form a suspension containing a precise dosage of the PPI. The suspension tablets of this invention comprise, in combination, a therapeutic amount of a PPI, a buffering agent, and a disintegrant. More particularly, the suspension tablets comprise about 20 mg omeprazole and about 1–20 mEq of sodium bicarbonate.

Croscarmellose sodium is a known disintegrant for tablet formulations, and is available from FMC Corporation, Philadelphia, Pa. under the trademark Ac-Di-Sol®. It is frequently blended in compressed tableting formulations either alone or in combination with microcrystalline cellulose to achieve rapid disintegration of the tablet.

Microcrystalline cellulose, alone or coprocessed with other ingredients, is also a common additive for compressed tablets and is well known for its ability to improve compressibility of difficult to compress tablet materials. It is commercially available under the Avicel® trademark. Two different Avicel® products are utilized, Avicel® PH which is microcrystalline cellulose, and Avicel® AC-815, a coprocessed spray dried residue of microcrystalline cellulose and a calcium, sodium alginate complex in which the calcium to sodium ratio is in the range of about 0.40:1 to about 2.5:1. While AC-815 is comprised of 85% microcrystalline cellulose (MCC) and 15% of a calcium, sodium alginate complex, for purposes of the present invention this ratio may be varied from about 75% MCC to 25% alginate up to about 95% MCC to 5% alginate. Depending on the particular formulation and active ingredient, these two components may be present in approximately equal amounts or in unequal amounts, and either may comprise from about 10% to about 50% by weight of the tablet.

The suspension tablet composition may, in addition to the ingredients described above, contain other ingredients often used in pharmaceutical tablets, including flavoring agents, sweetening agents, flow aids, lubricants or other common tablet adjuvants, as will be apparent to those skilled in the art. Other disintegrants, such as crospbvidone and sodium starch glycolate may be employed, although croscarmellose sodium is preferred.

In addition to the suspension tablet, the solid formulation of the present invention can be in the form of a powder, a tablet, a capsule, or other suitable solid dosage form (e.g., a pelleted form or an effervescing tablet, troche or powder), which creates the inventive solution in the presence of diluent or upon ingestion. For example, the water in the stomach secretions or water which is used to swallow the solid dosage form can serve as the aqueous diluent.

Compressed tablets are solid dosage forms prepared by compacting a formulation containing an active ingredient and excipients selected to aid the processing and improve the properties of the product. The term "compressed tablet" generally refers to a plain, uncoated tablet for oral ingestion, prepared by a single compression or by pre-compaction tapping followed by a final compression.

Such solid forms can be manufactured as is well known in the art. Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Lachman et al., *The Theory and Practice of Industrial Pharmacy* (1986). Such tablets may also comprise film coatings, which preferably dissolve upon oral ingestion or upon contact with diluent.

Non-limiting examples of buffering agents which could be utilized in such tablets include sodium bicarbonate, alkali earth metal salts such as calcium carbonate, calcium hydroxide, calcium lactate, calcium glycerophosphate, calcium acetate, magnesium carbonate, magnesium hydroxide, magnesium silicate, magnesium aluminate, aluminum hydroxide or aluminum magnesium hydroxide. A particular alkali earth metal salt useful for making an antacid tablet is calcium carbonate.

An example of a low density alkali earth metal salt useful for making the granules according to the present invention is extra light calcium carbonate available from Specialty Minerals Inc., Adams, Me. The density of the extra light calcium carbonate, prior to being processed according to the present invention, is about 0.37 gm/ml.

The granules used to make the tablets according to one embodiment of the present invention are made by either spray drying or pre-compacting the raw materials. Prior to being processed into granules by either process, the density of the alkali earth metal salts useful in the present invention ranges from about 0.3 gm/ml to about 0.55 gm/ml, preferably about 0.35 gm/ml to about 0.45 gm/ml, even more preferably about 0.37 gm/ml to about 0.42 gm/ml.

Additionally, the present invention can be manufactured by utilizing micronized compounds in place of the granules or powder. Micronization is the process by which solid drug particles are reduced in size. Since the dissolution rate is directly proportional to the surface area of the solid, and reducing the particle size increases the surface area, reducing the particle size increases the dissolution rate. Although micronization results in increased surface area possibly causing particle aggregation, which can negate the benefit of micronization and is an expensive manufacturing step, it does have the significant benefit of increasing the dissolution rate of relatively water insoluble drugs, such as omeprazole and other proton pump inhibitors.

The present invention also relates to administration kits to ease mixing and administration. A month's supply of powder or tablets, for example, can be packaged with a separate month's supply of diluent, and a re-usable plastic dosing cup. More specifically, the package could contain thirty (30) suspension tablets containing 20 mg omeprazole each, 1 L sodium bicarbonate 8.4% solution, and a 30 ml dose cup. The user places the tablet in the empty dose cup, fills it to the 30 ml mark with the sodium bicarbonate, waits for it to dissolve (gentle stirring or agitation may be used), and then ingests the suspension. One skilled in the art will appreciate that such kits may contain many different variations of the above components. For example, if the tablets or powder are compounded to contain PPI and buffering agent, the diluent may be water, sodium bicarbonate, or other compatible diluent, and the dose cup can be larger than 30 ml in size. Also, such kits can be packaged in unit dose form, or as weekly, monthly, or yearly kits, etc.

Although the tablets of this invention are primarily intended as a suspension dosage form, the granulations used to form the tablet may also be used to form rapidly disintegrating chewable tablets, lozenges, troches, or swallowable tablets. Therefore, the intermediate formulations as well as the process for preparing them provide additional novel aspects of the present invention.

Effervescent tablets and powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and tartaric acid. When the salts are added to water, the acids and the base react to liberate carbon dioxide gas, thereby causing "effervescence."

The choice of ingredients for effervescent granules. depends both upon the requirements of the manufacturing process and the necessity of making a preparation which dissolves readily in water. The two required ingredients are at least one acid and at least one base. The base releases carbon dioxide upon reaction with the acid. Examples of such acids include, but are not limited to, tartaric acid and citric acid. Preferably, the acid is a combination of both tartaric acid and citric acid. Examples of bases include, but are not limited to, sodium carbonate, potassium bicarbonate and sodium bicarbonate. Preferably, the base is sodium bicarbonate, and the effervescent combination has a pH of about 6.0 or higher.

Effervescent salts preferably include the following ingredients, which actually produce the effervescence: sodium bicarbonate, citric acid and tartaric acid. When added to water the acids and base react to liberate carbon dioxide, resulting in effervescence. It should be noted that any acid-base combination which results in the liberation of carbon dioxide could be used in place of the combination of sodium bicarbonate and citric and tartaric acids, as long as the ingredients were suitable for pharmaceutical use, and result in a pH of about 6.0 or higher.

It should be noted that it requires 3 molecules of $NaHCO_3$ (sodium bicarbonate) to neutralize 1 molecule of citric acid and 2 molecules of $NaHCO_3$ to neutralize 1 molecule of tartaric acid. It is desired that the approximate ratio of ingredients is as follows Citric Acid:Tartaric Acid:Sodium Bicarbonate=1:2:3.44 (by weight). This ratio can be varied and continue to produce an effective release of carbon dioxide. For example, ratios of about 1:0:3 or 0:1:2 are also effective.

The method of preparation of the effervescent granules of the present invention employs three basic processes: wet and dry granulation, and fusion. The fusion method is used for the preparation of most commercial effervescent powders. It should be noted that although these methods are intended for the preparation of granules, the formulations of effervescent salts of the present invention could also be prepared as tablets, according to well known prior art technology for tablet preparation.

Wet granulation is the oldest method of granule preparation. The individual steps in the wet granulation process of tablet preparation include milling and sieving of the ingredients; dry powder mixing; wet massing; granulation; and final grinding.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders; compressing (slugging); and grinding (slug reduction or granulation). No wet binder or moisture is involved in any of the steps.

The fusion method is the most preferred method for preparing the granules of the present invention. In this method, the compressing (slugging) step of the dry granulation process is eliminated. Instead, the powders are heated in an oven or other suitable source of heat.

PPIs Administered with Parietal Cell Activators

Applicant has unexpectedly discovered that certain compounds, such as chocolate, calcium and sodium bicarbonate and other alkaline substances, stimulate the parietal cells and enhance the pharmacologic activity of the PPI administered. For the purposes of this application, "parietal cell activator" shall mean any compound or mixture of compounds possessing such stimulatory effect including, but not limited to, chocolate, sodium bicarbonate, calcium (e.g., calcium carbonate, calcium gluconate, calcium hydroxide, calcium acetate and calcium glycerophosphate), peppermint oil, spearmint oil, coffee, tea and colas (even if decaffeinated), caffeine, theophylline, theobromine, and amino acids (particularly aromatic amino acids such as phenylalanine and tryptophan) and combinations thereof and the salts thereof.

Such parietal cell activators are administered in an amount sufficient to produce the desired stimulatory effect without causing untoward side effects to patients. For example, chocolate, as raw cocoa, is administered in an amount of about 5 mg to 2.5 g per 20 mg dose of omeprazole (or equivalent pharmacologic dose of other PPI). The dose of activator administered to a mammal, particularly a human, in the context of the present invention should be sufficient to effect a therapeutic response (i.e., enhanced effect of PPI) over a reasonable time frame. The dose will be determined by the strength of the particular compositions employed and the condition of the person, as well as the body weight of the person to be treated. The size of the dose also will be determined by the existence, nature, and extent of any adverse side effects that might accompany the administration of a particular composition.

The approximate effective ranges for various parietal cell activators per 20 mg dose of omeprazole (or equivalent dose of other PPI) are:

Chocolate (raw cocoa)—5 mg to 2.5 g

Sodium bicarbonate—7 mEq to 25 mEq

Calcium carbonate—1 mg to 1.5 Gm

Calcium gluconate—1 mg to 1.5 Gm

Calcium lactate—1 mg to 1.5 Gm

Calcium hydroxide—1 mg to 1.5 Gm

Calcium acetate—0.5 mg to 1.5 Gm

Calcium glycerophosphate—0.5 mg to 1.5 Gm

Peppermint oil—(powdered form) 1 mg to 1 Gm

Spearmint oil—(powdered form) 1 mg to 1 Gm

Coffee—20 ml to 240 ml

Tea—20 ml to 240 ml

Cola—20 ml to 240 ml

Caffeine—0.5 mg to 1.5 GM

Theophylline—0.5 mg to 1.5 GM

Theobromine—0.5 mg to 1.5 GM

Phenylalanine—0.5 mg to 1.5 GM

Tryptophan—0.5 mg to 1.5 GM

Pharmaceutically acceptable carriers are well-known to those who are skilled in the art. The choice of carrier will be determined, in part, both by the particular composition and by the particular method used to administer the composition. Accordingly, there is a wide variety of suitable formulations of the pharmaceutical compositions of the present invention.

EXAMPLE I

A. Fast Disintegrating Suspension Tablets of Omeprazole

A fast disintegrating tablet is compounded as follows: Croscarmellose sodium 300 g is added to the vortex of a rapidly stirred beaker containing 3.0 kg of deionized water. This slurry is mixed for 10 minutes. Omeprazole 90 g (powdered) is placed in the bowl of a Hobart mixer. After mixing, the slurry of croscarmellose sodium is added slowly to the omeprazole in the mixer bowl, forming a granulation which is then placed in trays and dried at 70° C. for three hours. The dry granulation is then placed in a blender, and to it is added 1,500 g of Avicel® AC-815 (85% microcrystalline cellulose coprocessed with 15% of a calcium, sodium alginate complex) and 1,500 g of Avicel® PH-302 (microcrystalline cellulose). After this mixture is thoroughly blended, 35 g of magnesium stearate is added and mixed for 5 minutes. The resulting mixture is compressed into tablets on a standard tablet press (Hata HS). These tablets have an average weight of about 1.5 g, and contain about 20 mg omeprazole. These tablets have low friability and rapid disintegration time. This formulation may be dissolved in an aqueous solution containing a buffering agent for immediate oral administration.

Alternatively, the suspension tablet may be swallowed whole with a solution of buffering agent. In both cases, the preferred solution is sodium bicarbonate 8.4%. As a further alternative, sodium bicarbonate powder (about 975 mg per 20 mg dose of omeprazole (or an equipotent amount of other PPI) is compounded directly into the tablet. Such tablets are then dissolved in water or sodium bicarbonate 8.4%, or swallowed whole with an aqueous diluent.

B. 10 mg Tablet Formula

| | |
|---|---|
| Omeprazole | 10 mg (or lansoprazole or pantoprazole or other PPI in an equipotent amount) |
| Calcium lactate | 175 mg |
| Calcium glycerophosphate | 175 mg |
| Sodium bicarbonate | 250 mg |
| Aspartame calcium (phenylalanine) | 0.5 mg |
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 3 mg |
| Mannitol | 3 mg |
| Pregelatinized starch | 3 mg |

C. 20 mg Tablet Formula

| | |
|---|---|
| Omeprazole | 20 mg (or lansoprazole or pantoprazole or other PPI in an equipotent amount) |
| Calcium lactate | 175 mg |
| Calcium glycerophosphate | 175 mg |
| Sodium bicarbonate | 250 mg |
| Aspartame calcium (phenylalanine) | 0.5 mg |
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 3 mg |
| Mannitol | 3 mg |
| Pregelatinized starch | 3 mg |

D. Tablet for Rapid Dissolution

| | |
|---|---|
| Omeprazole | 20 mg (or lansoprazole or pantoprazole or other PPI in an equipotent amount) |
| Calcium lactate | 175 mg |
| Calcium glycerophosphate | 175 mg |
| Sodium bicarbonate | 500 mg |
| Calcium hydroxide | 50 mg |
| Croscarmellose sodium | 12 mg |

E. Powder for Reconstitution for Oral Use (or per ng tube).

| | |
|---|---|
| Omeprazole | 20 mg (or lansoprazole or pantoprazole or other PPI in an equipotent amount) |
| Calcium lactate | 175 mg |
| Calcium glycerophosphate | 175 mg |
| Sodium bicarbonate | 500 mg |
| Calcium hydroxide | 50 mg |
| Glycerine | 200 g |

F. 10 mg Tablet Formula

| Omeprazole | 10 mg (or lansoprazole or pantoprazole or other PPI in an equipotent amount) |
|---|---|
| Calcium lactate | 175 mg |
| Calcium glycerophosphate | 175 mg |
| Sodium bicarbonate | 250 mg |
| Polyethylene glycol | 20 mg |
| Croscarmellose sodium | 12 mg |
| Peppermint | 3 mg |
| Magnesium silicate | 1 mg |
| Magnesium stearate | 1 mg |

G. 10 mg Tablet Formula

| Omeprazole | 10 mg (or lansoprazole or pantoprazole or other PPI in an equipotent amount) |
|---|---|
| Calcium lactate | 200 mg |
| Calcium glycerophosphate | 200 mg |
| Sodium bicarbonate | 400 mg |
| Croscarmellose sodium | 12 mg |
| Pregelatinized starch | 3 mg |

EXAMPLE II

Standard Tablet of PPI and Buffering Agent

Ten (10) tablets were prepared using a standard tablet press, each tablet comprising about 20 mg omeprazole and about 975 mg sodium bicarbonate uniformly dispersed throughout the tablet. To test the dissolution rate of the tablets, each was added to 60 ml of water. Using previously prepared liquid omeprazole/sodium bicarbonate solution as a visual comparator, it was observed that each tablet was completely dispersed in under three (3) minutes.

Another study using the tablets compounded according to this Example evaluated the bioactivity of the tablets in five (5) adult critical care patients. Each subject was administered one tablet via ng with a small amount of water, and the pH of ng aspirate was monitored using paper measure. The pH for each patient was evaluated for 6 hours and remained above 4, thus demonstrating the therapeutic benefit of the tablets in these patients.

Tablets were also prepared by boring out the center of sodium bicarbonate USP 975 mg tablets with a knife. Most of the removed sodium bicarbonate powder was then triturated with the contents of a 20 mg Prilosec® capsule and the resulting mixture was then packed into the hole in the tablet and sealed with glycerin.

EXAMPLE III

PPI Central Core Tablet

Tablets are prepared in a two-step process. First, about 20 mg of omeprazole is formed into a tablet as is known in the art to be used as a central core. Second, about 975 mg sodium bicarbonate USP is used to uniformly surround the central core to form an outer protective cover of sodium bicarbonate. The central core and outer cover are both prepared using standard binders and other excipients to create a finished, pharmaceutically acceptable tablet.

EXAMPLE IV

Effervescent Tablets and Granules

The granules of one 20 mg Prilosec® capsule were emptied into a mortar and triturated with a pestle to a fine powder. The omeprazole powder was then geometrically diluted with about 958 mg sodium bicarbonate USP, about 832 mg citric acid USP and about 312 mg potassium carbonate USP to form a homogeneous mixture of effervescent omeprazole powder. This powder was then added to about 60 ml of water whereupon the powder reacted with the water to create effervescence. A bubbling solution resulted of omeprazole and principally the antacids sodium citrate and potassium citrate. The solution was then administered orally to one adult male subject and gastric pH was measured using pHydrion paper. The results were as follows:

| Time Interval | pH Measured |
|---|---|
| Immediately prior to dose | 2 |
| 1 hour post dose | 7 |
| 2 hours post dose | 6 |
| 4 hours post dose | 6 |
| 6 hours post dose | 5 |
| 8 hours post dose | 4 |

One skilled in the art of pharmaceutical compounding will appreciate that bulk powders can be manufactured using the above ratios of ingredients, and that the a powder can be pressed into tablets using standard binders and excipients. Such tablets are then mixed with water to activate the effervescent agents and create the desired solution. In addition, lansoprazole 30 mg (or an equipotent dose of other PPI) can be substituted for omeprazole.

The effervescent powder and tablets can alternatively be formulated by employing the above mixture but adding an additional 200 mg of sodium bicarbonate USP to create a resulting solution with a higher pH. Further, instead of the excess 200 mg of sodium bicarbonate, 100 mg of calcium glycerophosphate or 100 mg of calcium lactate can be employed. Combinations of the same can also added.

EXAMPLE V

Parietal Cell Activator "Choco-Base™" Formulations and Efficacy

Children are affected by gastroesophageal reflux disease (GERD) with atypical manifestations. Many of these atypical symptoms are difficult to control with traditional drugs such as $H_2$-antagonists, cisapride, or sucralfate. PPIs are more effective in controlling gastric pH and the symptoms of GERD than other agents. However, PPIs are not available in dosage forms that are easy to administer to young children. To address this problem, applicant employed omeprazole or lansoprazole in a buffered chocolate suspension (Choco-Base, in children with manifestations of GERD.

Applicant performed a retrospective evaluation of children with GERD referred to the University of Missouri-Columbia from 1995 to 1998 who received treatment with the experimental omeprazole or lansoprazole Choco-Base suspension formulated in accordance with Formulation 1 stated below. Data were included on all patients with follow up information sufficient to draw conclusions about pre/post treatment (usually >6 months). There were 25 patients who met the criteria for this evaluation. Age range was several weeks to greater than 5 years. Most patients had a history of numerous unsuccessful attempts at ameliorating the effects of GERD. Medication histories indicated many trials of various drugs.

The primary investigator reviewed all charts for uniformity of data collection. When insufficient data was available in the University charts, attempts were made to review charts in the local primary care physicians' offices for follow-up data. If information was still unavailable to review, attempts were made to contact family for follow-up. If data were still unavailable the patients were considered inevaluable.

Patient charts were reviewed in detail. Data noted were date of commencement of therapy, date of termination of therapy and any reason for termination other than response to treatment. Patient demographics were also recorded, as were any other medical illnesses. Medical illnesses were divided grossly into those that are associated with or exacerbate GERD and those that do not.

Patient charts were examined for evidence of response to therapy. As this was largely a referral population, and a retrospective review, quantification of symptomatology based on scores, office visits and ED visits was difficult. Therefore, applicant examined charts for evidence of an overall change in patient symptoms. In specific, any data to point towards improvement, decline or lack of change were examined and recorded.

Results.

A total of 33 pediatric patients to date have been treated with the above-described suspension at the University of Missouri—Columbia. Of the 33 patients, 9 were excluded from the study, all based upon insufficient data about commencement, duration or outcome in treatment with PPI therapy. This left 24 patients with enough data to draw conclusions.

Of the 24 remaining patients, 18 were males and 6 females. Ages at implementation of PPI therapy ranged from 2 weeks of age to 9 years old. Median age at start of therapy was 26.5 months [mean of 37 mo.] Early on, reflux was usually documented by endoscopy and confirmed by pH probe. Eventually, pH probe was dropped and endoscopy was the sole method for documenting reflux, usually at the time of another surgery (most often T-tubes or adenoidectomy). Seven patients had pH probe confirmation of GERD, whereas 18 had endoscopic confirmation of reflux including all eight. who had pH probing done (See Graphs 1 and 2 below). Reflux was diagnosed on endoscopy most commonly by cobblestoning of the tracheal wall, with laryngeal and pharyngeal cobblestoning as findings in a few patients. Six patients had neither pH nor endoscopic documentation of GERD, but were tried on PPI therapy based on symptomatology alone.

Past medical history was identified in each chart. Ten patients had reflux-associated diagnoses. These were most commonly cerebral palsy, prematurity and Pierre Robin sequence. Other diagnoses were Charcot-Marie-Tooth disease, Velocardiofacial syndrome, Down syndrome and De George's syndrome. Non-reflux medical history was also identified and recorded separately (See Table 2 below). Patients were, in general, referral patients from local family practice clinics, pediatricians, or other pediatric health care professionals. Most patients were referred to ENT for upper airway problems, sinusitis, or recurrent/chronic otitis media that had been refractory to medical therapy as reported by the primary care physician. Symptoms and signs most commonly found in these patients were recorded and tallied. All signs and symptoms were broken down into six major categories: (1) nasal; (2) otologic; (3) respiratory; (4) gastrointestinal; (5) sleep-related; and (6) other. The most common problems fell into one or all of the first 3 categories (See Table 1 below).

Most patients had been treated in the past with medical therapy in the form of antibiotics, steroids, asthma medications and other diagnosis-appropriate therapies. In addition, nine of the patients had been on reflux therapy in the past, most commonly in the form of conservative therapy such as head of bed elevation 30°, avoidance of evening snacks, avoidance of caffeinated beverages as well as cisapride and ranitidine (See Graph 3 below).

The proton pump inhibitor suspension used in this group of patients was Choco-Base suspension of either lansoprazole or omeprazole. The dosing was very uniform, with patients receiving doses of either 10 or 20 mg of omeprazole and 23 mg of lansoprazole. Initially, in April of 1996 when therapy was first instituted 10 mg of omeprazole was used. There were 3 patients in this early phase who were treated initially with 10 mg po qd of omeprazole. All three subsequently were increased to either 20 mg po qd of omeprazole or 23 mg po qd of lansoprazole. All remaining patients were given either the 20 mg omeprazole or the 23 mg lansoprazole treatment qd, except in one case, where 30 mg of lansoprazole was used. Patients were instructed to take their doses once per day, preferably at night in most cases. Suspensions were all filled through the University of Missouri Pharmacy at Green Meadows. This allowed for tracking of usage through refill-data.

Most patients responded favorably to and tolerated the once daily dosing of Choco-Base proton pump inhibitor suspension. Two patients had documented adverse effects associated with the use of the PPI suspension. In one a patient, the mother reported increased burping up and dyspepsia, which was thought to be related to treatment failure. The other patient had small amounts of bloody stools per mother. This patient never had his stool tested, as his bloody stool promptly resolved upon cessation of therapy, with no further sequellae. The other 23 patients had no documented adverse effects.

Patients were categorized based on review of clinic notes and chart review into general categories: (1) improved; (2) unchanged; (3) failed; and (4) inconclusive. Of 24 patients with sufficient data for follow up, 18 showed improvement in symptomatology upon commencement of PPI therapy [72%]. The seven who did not respond were analyzed and grouped. Three showed no change in symptomatology and clinical findings while on therapy, one complained of worsening symptoms while on therapy, one patient had therapy as prophylaxis for surgery, and two stopped therapy just after its commencement (see graph 4). Setting aside the cases in which therapy was stopped before conclusions could be drawn and the case in which PPI therapy was for purely prophylactic reasons, leaves (17/21) 81% of patients that responded to Choco-Base suspension. This means that 19% (4/21) of patients received no apparent benefit from PPI therapy. Of all these patients, only 4% complained of worsening symptoms and the side effects were 4% (1/21) and were mild bloody stool that completely resolved upon cessation of therapy.

Discussion.

GERD in the pediatric population is relatively common, affecting almost 50% of newborns. Even though most infants outgrow physiologic reflux, pathologic reflux still affects approximately 5% of all children, throughout childhood. Recently considerable data has pointed to reflux as an etiologic factor in extra-esophageal areas. GERD has been attributed to sinusitis, dental caries, otitis media, asthma, apnea, arousal, pneumonia, bronchitis, and cough, among others. Despite the common nature of reflux, there seems to have been little improvement in therapy for reflux, especially in the non-surgical arena.

The standard of therapy for the treatment of GERD in the pediatric population has become a progression from conservative therapy to a combination of a pro-kinetic agent and H-2 blocker therapy. Nonetheless, many patients fail this treatment protocol and become surgical candidates. In adults, PPI therapy is effective in 90% of those treated for gastroesophageal reflux disease. As a medical alternative to the H-2 blockers, the proton pump inhibitors have not been studied extensively in the pediatric population. Part of the reason for this lack of data may be related to the absence of a suitable dosage formulation for this very young population, primarily under 2 years of age, that does not swallow capsules or tablets. It would be desirable to have a true liquid formulation (solution or suspension) with good palatability such as is used for oral antibiotics, decongestants, antihistamines, H-2 blockers, cisapride, metoclopramide, etc. The use of lansoprazole granules (removed from the gelatin capule) and sprinkled on applesauce has been approved by the Food and Drug Administration as an alternative method of drug administration in adults but not in children. Published data are lacking on the efficacy of the lansoprazole sprinkle method in children. Omeprazole has been studied for bioequivalence as a sprinkle in adults and appears to produce comparable serum concentrations when compared to the standard capsule. Again no data are available on the omeprazole sprinkle in children. An additional disadvantage of omeprazole is its taste which is quinine-like. Even when suspended in juice, applesauce or the like, the bitter nature of the medicine is easily tasted even if one granule is chewed. For this reason applicant eventually progressed to use lansoprazole in Choco-Base. Pantoprazole and rabeprazole are available as enteric-coated tablets only. Currently, none of the proton pump inhibitors available in the United States are approved for pediatric use. There is some controversy as to what the appropriate dosage should be in this group of patients. A recent review by Israel D., et al. suggests that effective PPI dosages should be higher than that originally reported, i.e., from 0.7 mg/kg to 2 or 3 mg/kg omeprazole. Since toxicity with the PPI's is not seen even at >50 mg/kg, there appears little risk associated with the higher dosages. Based on observations at the University of Missouri consistent with the findings of this review, applicant established a simple fixed dosage regimen of 10 ml Choco-Base suspension daily. This 10 ml dose provided 20 mg omeprazole and 23 mg lansoprazole.

In the ICU setting, the University of Missouri-Columbia has been using an unflavored PPI suspension given once daily per various tubes (nasogastric, g-tube, jejunal feeding tube, duo tube, etc.) for stress ulcer prophylaxis. It seemed only logical that if this therapy could be made into a palatable form, it would have many ideal drug characteristics for the pediatric population. First, it would be liquid, and therefore could be administered at earlier ages. Second, if made flavorful it could help to reduce noncompliance. Third, it could afford once daily dosing, also helping in reducing noncompliance. In the process, applicant discovered that the dosing could be standardized, which nearly eliminated dosing complexity.

Choco-Base is a product which protects drugs which are acid labile, such as proton pump inhibitors, from acid degradation. The first few pediatric patients with reflux prescribed Choco-Base were sicker patients. They had been on prior therapy and had been diagnosed both by pH probe and endoscopy. In the first few months, applicant treated patients with 10 mg of omeprazole qd (1 mg/kg) and found this to be somewhat ineffective, and quickly increased the dosing to 20 mg (2 mg/kg) of omeprazole. About halfway through the study, applicant began using lansoprazole 23 mg po qd. Applicant's standard therapy was then either 20 mg of omeprazole or 23 mg of lansoprazole once daily. The extra 3 mg of lansoprazole is related only to the fact that the final concentration was 2.25 mg/ml, and applicant desired to keep dosing simple, so he used a 10 ml suspension.

The patients that were treated represented a tertiary care center population, and they were inherently sicker and refractory to medical therapy in the past. The overall 72% success rate is slightly lower than the 90% success rates of PPIs in the adult population, but this can be attributed to the refractory nature of their illness, most having failed prior non-PPI treatment. The population in this study is not indicative of general practice populations.

Conclusion.

PPI therapy is a beneficial therapeutic option in the treatment of reflux related symptoms in the pediatric population. Its once daily dosing and standard dosing scheme combined with a palatable formulation makes it an ideal pharmacologic agent.

TABLE 1

| Symptoms | Patient Numbers |
| --- | --- |
| Nasal: | 35 |
| Sinusitis | 7 |
| Congestion | 8 |
| Nasal discharge | 16 |
| Other | 4 |
| Otologic: | 26 |
| Otitis Media | 17 |
| Otorrhea | 9 |
| Respiratory: | 34 |
| Cough | 10 |
| Wheeze | 11 |
| Respiratory Distress: | 5 |
| Pneumonia | 2 |
| Other | 6 |
| Gastrointestinal: | 10 |
| Abdominal Pain | 1 |
| Reflux/Vomiting | 4 |
| Other | 4 |
| Sleep Disturbances: | 11 |
| Other | 2 |

TABLE 2

| Past Medical History | Number of Patients |
| --- | --- |
| Reflux Associated: | 12 |
| Premature | 5 |
| Pierre-Robin | 2 |
| Cerebral Palsy | 2 |
| Down Syndrome | 1 |
| Charcot-Marie-Tooth | 1 |
| Velocardiofacial Syndrome | 1 |
| Other Medical History | 12 |
| Cleft Palate | 3 |
| Asthma | 3 |
| Autism | 2 |
| Seizure Disorder | 1 |
| Diabetes Mellitus | 1 |
| Subglottic Stenosis | 1 |
| Tracheostomy Dependent | 1 |

FORMULATION 1

| PART A INGREDIENTS | AMOUNT (mg) |
| --- | --- |
| Omeprazole | 200 |
| Sucrose | 26000 |
| Sodium Bicarbonate | 9400 |
| Cocoa | 1800 |
| Corn Syrup Solids | 6000 |
| Sodium Caseinate | 1000 |
| Soy Lecithin | 150 |

-continued

| | |
|---|---|
| Sodium Chloride | 35 |
| Tricalcium Phosphate | 20 |
| Dipotassium Phosphate | 12 |
| Silicon Dioxide | 5 |
| Sodium Stearoyl Lactylate | 5 |

| PART B INGREDIENTS | AMOUNT (ml) |
|---|---|
| Distilled Water | 100 |

COMPOUNDING INSTRUCTIONS

Add Part B to Part A to create a total volume of approximately 130 ml with an omeprazole concentration of about 1.5 mg/ml.

FORMULATION 2

| PART A INGREDIENTS (mg) | AMOUNT (mg) |
|---|---|
| Sucrose | 26000 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |

| PART B INGREDIENTS | AMOUNT |
|---|---|
| Distilled Water | 100 ml |
| Sodium Bicarbonate | 8400 mg |
| Omeprazole | 200 mg |

COMPOUNDING INSTRUCTIONS

Mix the constituents of Part B together thoroughly and then add to Part A. This results in a total volume of approximately 130 ml with an omeprazole concentration of about 1.5 mg/ml.

FORMULATION 3

| PART A INGREDIENTS (mg) | AMOUNT (mg) |
|---|---|
| Sucrose | 26000 |
| Sodium Bicarbonate | 9400 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |

| PART B INGREDIENTS | AMOUNT |
|---|---|
| Distilled Water | 100 ml |
| Omeprazole | 200 mg |

COMPOUNDING INSTRUCTIONS

This formulation is reconstituted at the time of use by a pharmacist. Part B is mixed first and is then uniformly mixed with the components of Part A. A final volume of about 130 ml is created having an omeprazole concentration of about 1.5 mg/ml.

FORMULATION 4

| PART A INGREDIENTS (mg) | AMOUNT (mg) |
|---|---|
| Sucrose | 26000 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |

| PART B INGREDIENTS | AMOUNT |
|---|---|
| Distilled Water | 100 ml |
| Sodium Bicarbonate | 8400 mg |
| Omeprazole | 200 mg |

COMPOUNDING INSTRUCTIONS

This formulation is reconstituted at the time of use by a pharmacist. Part B is mixed first and is then uniformly mixed with the components of Part A. A final volume of about 130 ml is created having an omeprazole concentration of about 1.5 mg/ml.

In all four of the above formulations, lansoprazole or other PPI can be substituted for omeprazole in equipotent amounts. For example, 300 mg of lansoprazole may be substituted for the 200 mg of omeprazole. Additionally, aspartame can be substituted for sucrose, and the following other ingredients can be employed as carriers, adjuvants and excipients: maltodextrin, vanilla, carragreenan, mono and diglycerides, and lactated monoglycerides. One skilled in the art will appreciate that not all of the ingredients are necessary to create a Choco-Base formulation that is safe and effective.

Omeprazole powder or enteric coated granules can be used in each formulation. If the enteric coated granules are used, the coating is either dissolved by the aqueous diluent or inactivated by trituration in the compounding process.

Applicant additionally analyzed the effects of a lansoprazole Choco-Base formulation on gastric pH using a pH meter (Fisher Scientific) in one adult patient versus lansoprazole alone. The patient was first given a 30 mg oral capsule of Prevacid®, and the patient's gastric pH was measured at 0, 4, 8, 12, and 16 hours post dose. The results are illustrated in FIG. 4.

The Choco-Base product was compounded according to Formulation 1 above, except 300 mg of lansoprazole was used instead of omeprazole. A dose of 30 mg lansoprazole Choco-Base was orally administered at hour 18 post lansoprazole alone. Gastric pH was measured using a pH meter at hours 18, 19, 24, 28, 32, 36, 40, 48, 52, and 56 post lansoprazole alone dose.

Figure 4:
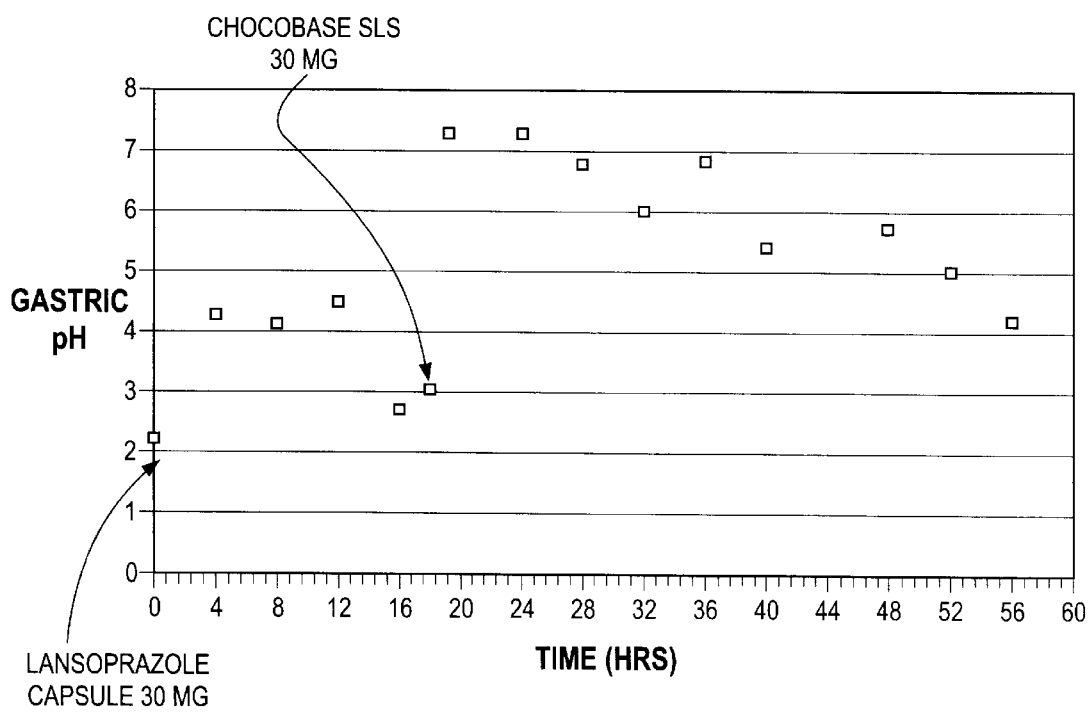
FIG. 4 is a graph illustrating the stomach pH values after the oral administration of both chocolate plus lansoprazole and lansoprazole alone.

FIG. 4 illustrates the lansoprazole/cocoa combination resulted in higher $pH_s$ at hours 19–56 than lansoprazole alone. at hours 4–18. Therefore, the combination of the lansoprazole with chocolate enhanced the pharmacologic activity of the lansoprazole. The results establish that the sodium bicarbonate as well as chocolate flavoring and calcium were all able to stimulate the activation of the proton pumps, perhaps due to the release of gastrin. Proton pump inhibitors work by functionally inhibiting the proton pump and effectively block activated proton pumps (primarily those inserted into the secretory canalicular membrane) By further administering the proton pump inhibitor with one of these activators or enhancers, there is a synchronization of activation of the proton pump with the absorption and subsequent parietal cell concentrations of the proton pump inhibitor. As illustrated in FIG. 4, this combination produced a much longer pharmacologic effect than when the proton pump inhibitor was administered alone.

EXAMPLE VI

Combination Tablet Delivering Bolus and Time-released Doses of PPI

Tablets were compounded using known methods by forming an inner core of 10 mg omeprazole powder mixed with 750 mg sodium bicarbonate, and an outer core of 10 mg omeprazole enteric-coated granules mixed with known binders and excipients. Upon ingestion of the whole tablet, the tablet dissolves and the inner core is dispersed in the stomach where it is absorbed for immediate therapeutic effect. The enteric-coated granules are later absorbed in the duodenum to provide symptomatic relief later in the dosing cycle. This tablet is particularly useful in patients who experience breakthrough gastritis between conventional doses, such as while sleeping or in the early morning hours.

EXAMPLE VII

Therapeutic Application

Patients were evaluable if they met the following criteria: had two or more risk factors for SRMD (mechanical ventilation, head injury, severe burn, sepsis, multiple, trauma, adult respiratory distress syndrome, major surgery, acute renal failure, multiple operative procedures, coagulotherapy, significant hyportension, acid-base disorder, and hepatic failure), gastric pH of ≦4 prior to study entry, and no concomitant prophylaxis for SRMD.

The omeprazole solution was prepared by mixing 10 ml of 8.4% sodium bicarbonate with the contents of a 20 mg capsule of omeprazole (Merck & Co.. Inc., West Point, Pa.) to yield. a solution having a final omeprazole concentration of 2 mg/ml.

Nasogastric (ng) tubes were placed in the patients and an omeprazole dosage protocol of buffered 40 mg omeprazole solution (2 mg omeprazole/1 ml NaHCO$_3$—8.4%) followed by 40 mg of the same buffered omeprazole solution in eight hours, then 20 mg of the same buffered omeprazole solution per day, for five days. After each buffered omeprazole solution administration, nasogastric suction was turned off for thirty minutes.

Eleven patients were evaluable. All patients were mechanically ventilated. Two hours after the initial 40 mg dose of buffered omeprazole solution, all patients had an increase in gastric pH to greater than eight as shown in FIG. 1. Ten of the eleven patients maintained a gastric pH of greater than or equal to four when administered 20 mg omeprazole solution. One patient required 40 mg omeprazole solution per day (closed head. injury, five total risk factors for SRMD). Two patients were changed to omeprazole solution after having developed clinically significant upper gastrointestinal bleeding while receiving conventional intravenous H$_2$-antagonists. Bleeding subsided in both cases after twenty-four hours. Clinically significant upper gastrointestinal bleeding did not occur in the other nine patients. Overall mortality was 27%, mortality attributable to upper gastrointestinal bleeding was 0%. Pneumonia developed in one patient after initiating omeprazole therapy and was present upon the initiation of omeprazole therapy in another patient. The mean length of prophylaxis was five days.

A pharmacoeconomic analysis revealed a difference in the total cost of care for the prophylaxis of SRMD:

ranitidine (Zantac®) continuous infusion intravenously (150 mg/24 hours)×five days $125.50;

cimetidine (Tagamet®) continuous infusion intravenously (900 mg/24 hours)×five days $109.61;

sucralfate one gm slurry four times a day per (ng) tube× five days $73.00; and buffered omeprazole solution regimen per (ng) tube×five days $65.70.

This example illustrates the efficacy of the buffered omeprazole solution of the present invention based on the increase in gastric pH, safety and cost of the buffered omeprazole solution as a method for SRMD prophylaxis.

EXAMPLE VIII

Effect on pH

Experiments were carried out in order to determine the effect of the omeprazole solution (2 mg omeprazole/1 ml NaHCO$_3$—8.4%) administration on the accuracy of subsequent pH measurements through a nasogastric tube.

After preparing a total of 40 mg of buffered omeprazole solution, in the manner of Example VII, doses were administered into the stomach, usually, through a nasogastric (ng) tube. Nasogastric tubes from nine different institutions were gathered for an evaluation. Artificial gastric fluid (gf) was prepared according to the USP. pH recordings were made in triplicate using a Microcomputer Portable pH meter model 6007 (Jenco Electronics Ltd., Taipei, Taiwan).

First, the terminal portion (tp) of the nasogastric tubes was placed into a glass beaker containing the gastric fluid. A 5 ml aliquot of gastric fluid was aspirated through each tube and the pH recorded; this was called the "pre-omeprazole solution/suspension measurement." Second, the terminal portion (tp) of each of the nasogastric tubes was removed from the beaker of gastric fluid and placed into an empty beaker. Twenty (20) mg of omeprazole solution was delivered through each of the nasogastric tubes and flushed with 10 ml of tap water. The terminal portion (tp) of each of the nasogastric tubes was placed back into the gastric fluid. After a one hour incubation, a 5 ml aliquot of gastric fluid was aspirated through each nasogastric tube and the pH recorded; this was called the "after first dose SOS [Simplified Omeprazole Solution] measurement." Third, after an additional hour had passed, the second step was repeated; this was called the "after second dose SOS [Simplified Omeprazole Solution] measurement." In addition to the pre-omeprazole measurement, the pH of the gastric fluid was checked in triplicate after the second and third steps. A change in the pH measurements of +/− 0.3 units was considered significant. The Friedman test was used to compare the results. The Friedman test is a two way analysis of variance which is used when more than two related samples are of interest, as in repeated measurements.

The results of these experiments are outlined in Table 1.

TABLE 1

|  | ng1 | ng2 | ng3 | ng4 | ng5 | ng6 | ng7 | ng8 | ng9 |
|---|---|---|---|---|---|---|---|---|---|
| [1] gf Pre SOS | 1.3 | 1.3 | 1.3 | 1.3 | 1.3 | 1.3 | 1.3 | 1.3 | 1.3 |
| [2] gf p 1st dose 1.3←check of fg pH | 1.3 | 1.3 | 1.3 | 1.3 | 1.3 | 1.3 | 1.3 | 1.3 | 1.3 |
| [3] gf p 2nd Dose 1.3←check of gf pH | 1.3 | 1 3 | 1.4 | 1.4 | 1.4 | 1.3 | 1.4 | 1.3 | 1.3 |

SOS pH = 9.0

Table 1 illustrates the results of the pH measurements that were taken during the course of the experiment. These results illustrate that there were no statistically significant latent effects of omeprazole solution administration (per nasogastric tube) on the accuracy of subsequent pH measurements obtained through the same nasogastric tube.

EXAMPLE IX

Efficacy of Buffered Omeprazole Solution in Ventilated Patients

Experiments were performed in order to determine the efficacy, safety, and cost of buffered omeprazole solution in mechanically ventilated critically ill patients who have at least one additional risk factor for stress-related mucosal damage.

Patients: Seventy-five adult, mechanically ventilated patients with at least one additional risk factor for stress-related mucosal damage.

Interventions: Patients received 20 ml omeprazole solution (prepared as per Example VII and containing 40 mg of omeprazole) initially, followed by a second 20 ml dose six to eight hours later, then 10 ml (20 mg) daily. Omeprazole solution according to the present invention was administered through a nasogastric tube, followed by 5–10 ml of tap water. The nasogastric tube was clamped for one to two hours after each administration.

Measurements and Main Results: The primary outcome measure was clinically significant gastrointestinal bleeding determined by endoscopic evaluation, nasogastric aspirate examination, or heme-positive coffee ground material that did not clear with lavage and was associated with a five percent decrease in hematocrit. Secondary efficacy measures were gastric pH measured four hours after omeprazole was first administered, mean gastric pH after omeprazole was started, and the lowest gastric pH during omeprazole therapy. Safety-related outcomes included the incidence of adverse events and the incidence of pneumonia. No patient experienced clinically significant upper gastrointestinal bleeding after receiving omeprazole suspension. The four-hour post omeprazole gastric pH was 7.1 (mean), the mean gastric pH after starting omeprazole was 6.8 (mean) and the lowest pH after starting omeprazole was 5.6 (mean). The incidence of pneumonia was twelve percent. No patient in this high-risk population experienced an adverse event or a drug interaction that was attributable to omeprazole.

Conclusions: Omeprazole solution prevented clinically significant upper, gastrointestinal bleeding and maintained gastric pH above 5.5 in mechanically ventilated critical care patients without producing toxicity.

Materials and Methods

The study protocol was approved by the Institutional Review Board for the University of Missouri at Columbia.

Study Population: All adult (>18 years old) patients admitted to the surgical intensive care and burn unit at the University of Missouri Hospital with an intact stomach, a nasogastric tube in place, and an anticipated intensive care unit stay of at least forty-eight hours were considered for inclusion in the study. To be included patients also had to have a gastric pH of <4, had to be mechanically ventilated and have one of the following additional risk factors for a minimum of twenty-four hours after initiation of omeprazole suspension: head injury with altered level of consciousness, extensive burns (>20% Body Surface Area), acute renal failure, acid-base disorder, multiple trauma, coagulopathy, multiple operative procedures, coma, hypotension for longer than one hour or sepsis (see Table 2). Sepsis was defined as the presence of invasive. pathogenic organisms or their toxins in blood or tissues resulting in a systematic response that included two or more of the following: temperature greater than 38° C. or less than 36° C., heart rate greater than 90 beats/minute, respiratory rate greater than 20 breaths/minute (or $pO_2$ less than 75 mm Hg), and white blood cell count greater than 12,000 or less than 4,000 cells/mm$^3$ or more than 10 percent bands (Bone, Let's Agree on Terminology: Definitions of Sepsis, Crit. Care Med., 19: 27 (1991)). Patients in whom $H_2$-antagonist therapy had failed or who experienced an adverse event while receiving $H_2$-antagonist therapy were also included.

Patients were excluded from the study if they were receiving azole antifungal agents through the nasogastric tube; were likely to swallow blood (e.g., facial and/or sinus fractures, oral lacerations); had severe thrombocytopenia (platelet count less than 30,000 cells/mm$^3$) ; were receiving enteral feedings through the nasogastric tube; or had a history of vagotomy, pyloroplasty, or gastroplasty. In addition, patients with a gastric pH above four for forty-eight hours after ICU admission (without, prophylaxis) were not eligible for participation. Patients who developed bleeding within the digestive tract that was not stress-related mucosal damage (e.g., endoscopically verified variceal bleeding or Mallory-Weiss tears, oral lesions, nasal tears due to placement of the nasogastric tube) were excluded from the efficacy evaluation and categorized as having non-stress-related mucosal bleeding. The reason for this exclusion is the confounding effect of non-stress-related mucosal bleeding on efficacy-related outcomes, such as the use of nasogastric aspirate inspection to define clinically significant upper gastrointestinal bleeding.

Study Drug Administration: Omeprazole solution was prepared immediately before administration by the patient's nurse using the following instructions: empty the contents of one or two 20 mg omeprazole capsule(s) into an empty 10 ml syringe (with 20 gauge needle in place) from which the plunger has been removed. (Omeprazole delayed-release capsules, Merck & Co., Inc., West Point, Pa.); replace the plunger and uncap the needle; withdraw 10 ml of 8.4% sodium bicarbonate solution or 20 ml if 40 mg given (Abbott Laboratories, North Chicago, Ill.), to create a concentration of 2 mg omeprazole per ml of 8.4% sodium bicarbonate; and allow the enteric coated pellets of omeprazole to completely breakdown, 30 minutes (agitation is helpful). The omeprazole in the resultant preparation is partially dissolved and partially suspended. The preparation should have a milky white appearance with fine sediment and should be shaken before administration. The solution was not administered with acidic substances. A high pressure liquid chromatography study was performed that demonstrated that this preparation of simplified omeprazole suspension maintains >90% potency for seven days at room temperature. This preparation remained free of bacterial and fungal contamination for thirty days when stored at room temperature (See Table 5).

The initial dose of omeprazole solution was 40 mg, followed by a second 40 mg dose six to eight hours later, then a 20 mg daily dose administered at 8:00 AM. Each dose was administered through the nasogastric tube. The nasogastric tube was then flushed with 5–10 ml of tap water and clamped for at least one hour. Omeprazole therapy was continued until there was no longer a need for stress ulcer prophylaxis (usually after the nasogastric tube was removed and the patient was taking water/food by mouth, or after the patient was removed from mechanical ventilation).

Primary Outcome Measures: The primary outcome measure in this study was the rate of clinically significant stress-related mucosal bleeding defined as endoscopic evidence of stress-related mucosal bleeding or bright red blood per nasogastric tube that did not clear after a 5-minute lavage or persistent Gastroccult (SmithKline Diagnostics, Sunnyville, Calif.) positive coffee ground material for four consecutive hours that did not clear with lavage (at least 100 ml) and produced a 5% decrease in hematocrit.

Secondary Outcome Measures: The secondary efficacy measures were gastric pH measured four hours after omeprazole was administered, mean gastric pH after starting omeprazole and lowest gastric pH during omeprazole administration. Gastric pH was measured immediately after aspirating gastric contents through the nasogastric tube. pH paper (pHydrion improved pH papers, Microessential Laboratory, Brooklyn, N.Y.) was used to measure gastric aspirate pH. The pH range of the test strips was 1 to 11, in increments of one pH unit. Gastric pH was measured before the initiation of omeprazole solution therapy, immediately before each dose, and every four hours between doses.

Other secondary outcome measures were incidence of adverse events (including drug interactions) and pneumonia. Any adverse event that developed during the study was recorded. Pneumonia was defined using indicators adapted from the Centers for Disease Prevention and Control definition of nosocomial pneumonia (Garner et al., 1988). According to these criteria, a patient who has pneumonia is one who has rales or dullness to percussion on physical examination of the chest or has a chest radiograph that shows new or progressive infiltrate(s), consolidation, cavitation, or pleural effusion and has at least two of the following present: new purulent sputum or changes in character of the sputum, an organism isolated from blood culture, fever or leukocytosis, or evidence of infection from a protective specimen brush or bronchoalveolar lavage. Patients who met the criteria for pneumonia and were receiving antimicrobial agents for the treatment of pneumonia were included in the pneumonia incidence figure. These criteria were also used as an initial screen before the first dose of study drug was administered to determine if pneumonia was present prior to the start of omeprazole suspension.

Cost of Care Analysis: A pharmacoeconomic evaluation of stress ulcer prophylaxis using omeprazole solution was performed. The evaluation included total drug cost (acquisition and administration), actual costs associated with adverse events (e.g., psychiatry consultation for mental confusion), costs associated with clinically significant upper gastrointestinal bleeding. Total drug cost was calculated by adding the average institutional costs of omeprazole 20 mg capsules, 50 ml sodium bicarbonate vials, and 10 ml syringes with needle; nursing time (drug administration, pH monitoring); pharmacy time (drug preparation); and disposal costs. Costs associated with clinically significant upper gastrointestinal bleeding included endoscopy charges and accompanying consultation fees, procedures required to stop the bleeding (e.g., surgery, hemostatic agents, endoscopic procedures), increased hospital length of stay (as assessed by the attending physician), and cost of drugs used to treat the gastrointestinal bleeding.

Statistical Analysis: The paired t-test (two-tailed) was used to compare gastric pH before and after omeprazole solution administration and to compare gastric pH before omeprazole solution administration with the mean and lowest gastric pH value measured after beginning omeprazole.

Figure 2:
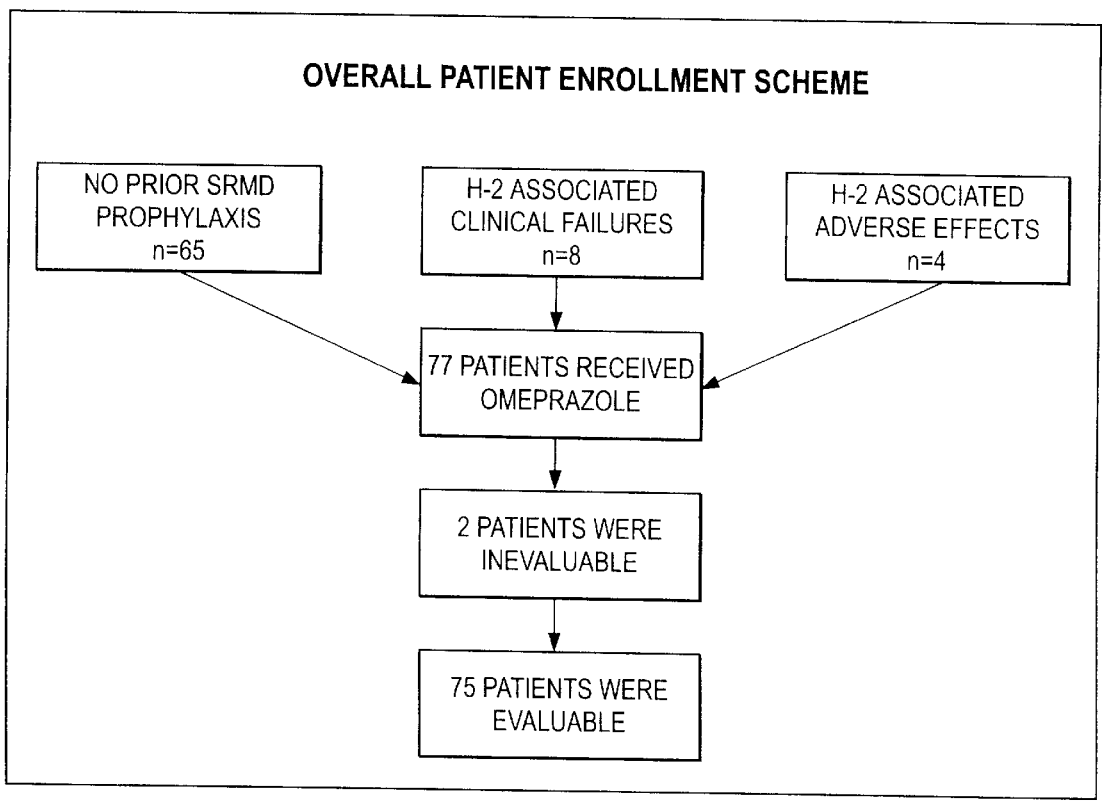
FIG. 2 is a flow chart illustrating a patient enrollment scheme.

Results:

Seventy-seven patients met the inclusion and exclusion criteria and received omeprazole solution (See FIG. 2). Two patients were excluded from the efficacy evaluation because the protocol for omeprazole administration was not followed. In one case, the omeprazole enteric-coated pellets had not completely broken down prior to the administration of the first two doses, which produced an erratic effect on gastric pH. The gastric pH increased to above six as soon as the patient was given a dose of omeprazole solution (in which the enteric coated pellets of omeprazole had been allowed to completely breakdown).

The reason for the second exclusion was that nasogastric suctioning was not turned off after the omeprazole dose was administered. This resulted in a transient effect on gastric pH. The suction was turned off with subsequent omeprazole doses, and control of gastric pH was achieved. Two patients were considered efficacy failures because omeprazole failed to maintain adequate gastric pH control on the standard omeprazole 20 mg/day maintenance dose. When the omeprazole dose was increased to 40 mg/day (40 mg once/day or 20 mg twice/day), gastric pH was maintained above four in both patients. These two patients were included in the safety and efficacy evaluations, including the gastric pH analysis. After the two patients were declared failures, their pH values were no longer followed.

The ages of the remaining seventy-five patients ranged from eighteen to eighty-seven years; forty-two patients were male and thirty-three were female. All patients were mechanically ventilated during the study. Table 2 shows the frequency of risk factors for stress-related bleeding that were exhibited by the patients in this study. The most common risk factors in this population were mechanical ventilation and major surgery. The range of risk factors for any given patient was two to ten, with a mean of 3 (±1) (standard deviation). Five patients enrolled in the study had developed clinically significant bleeding while receiving continuous infusions of ranitidine (150 mg/24 hr) or cimetidine (900 mg/24 hr). In all five cases, the bleeding subsided and the gastric pH rose to above five within thirty-six hours after initiating omeprazole therapy. Three patients were enrolled after having developed two consecutive gastric pH values below three while receiving an $H_2$-antagonist (in the doses outlined above). In all three cases, gastric pH rose to above five within four hours after omeprazole therapy was initiated. Four other patients were enrolled in this study after experiencing confusion (n=2) or thrombocytopenia (n=2) during $H_2$-antigens therapy. Within thirty-six hours of switching therapy, these adverse events resolved.

Stress-related Mucosal Bleeding and Mortality: None of the sixty-five patients who received buffered omeprazole solution as their initial prophylaxis against stress-related mucosal bleeding developed overt or clinically significant upper gastrointestinal bleeding. In four of the five patients who had developed upper gastrointestinal bleeding before study entry, bleeding diminished to the presence of occult blood only (Gastroccult-positive) within eighteen hours of starting omeprazole solution; bleeding stopped in all patients within thirty-six hours. The overall mortality rate in this group of critically ill patients was eleven percent. No death was attributable to upper gastrointestinal bleeding or the use of omeprazole solution.

Figure 3:
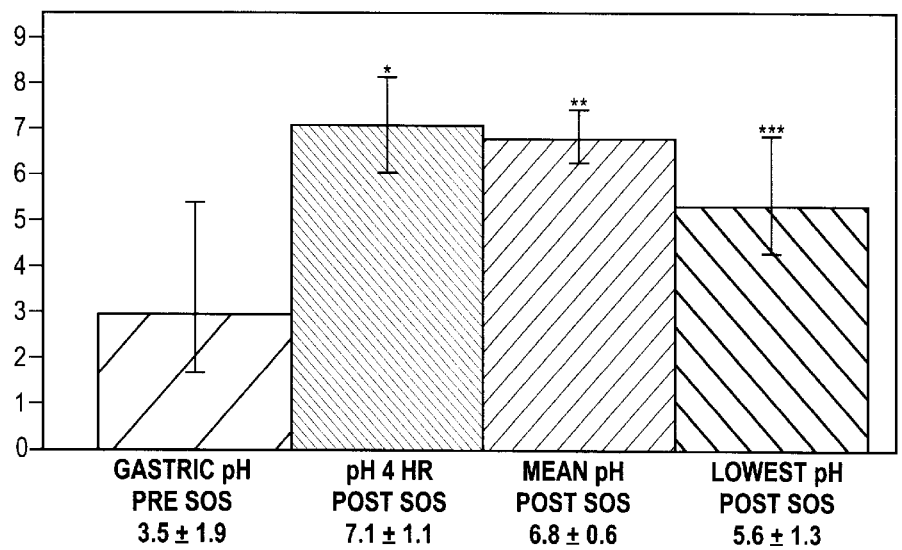
FIG. 3 is a bar graph illustrating gastric pH both pre- and post-administration of omeprazole solution according to the present invention.

Gastric pH: The mean (±standard deviation) pre-omeprazole gastric pH was 3.5±1.9. Within four hours of omeprazole administration, the gastric pH rose to 7.1±1.1 (See FIG. 3); this difference was significant (p<0.001). The differences between pre-omeprazole gastric pH and the mean and lowest gastric pH measurements during omeprazole administration (6.8±0.6 and 5.6±1.3, respectively) were also statistically significant (p<0.001).

Safety: Omeprazole solution was well tolerated in this group of critically ill patients. Only one patient with sepsis experienced an adverse event that may have been drug-related thrombocytopenia. However, the platelet count continued to fall after omeprazole was stopped. The platelet count then returned to normal despite reinstitution of omeprazole therapy. Of note, one patient on a jet ventilator continuously expelled all liquids placed in her stomach up and out through her mouth, and thus was unable to continue on omeprazole. No. clinically. significant drug interactions with omeprazole were noted during the study period. As stated above, metabolic alkalosis is a potential concern in patients receiving sodium bicarbonate. However, the amount of sodium bicarbonate in omeprazole solution was small (12 mEq/10 ml) and no electrolyte abnormalities were found.

Pneumonia: Pneumonia developed in nine (12%) patients receiving omeprazole solution. Pneumonia was present in an additional five patients before the start of omeprazole therapy.

Pharmacoeconomic evaluation: The average length of treatment was nine days. The cost of care data are listed in Tables 3 and 4. The costs of drug acquisition, preparation, and delivery for some of the traditional agents used in the prophylaxis of stress-related upper gastrointestinal bleeding are listed in Table 3. There were no costs to add from toxicity associated with omeprazole solution. Since two of seventy-five patients required 40 mg of omeprazole solution daily to adequately control gastric pH, the acquisition/preparation cost should reflect this. The additional 20 mg of omeprazole with vehicle adds seven cents per day to the cost of care. Therefore, the daily cost of care for omeprazole solution in the prophylaxis of stress-related mucosal bleeding was $12.60 (See Table 4).

Omeprazole solution is a safe and effective therapy for the prevention of clinically significant stress-related mucosal bleeding in critical care patients. The contribution of many risk factors to stress-related mucosal damage has been challenged recently. All of the patients in this study had at least one risk factor that has clearly been associated with stress-related mucosal damage—mechanical ventilation. Previous trials and data from a recently published study show that stress ulcer prophylaxis is of proven benefit in patients at risk and, therefore, it was thought to be unethical to include a placebo group in this study. No clinically significant upper gastrointestinal bleeding occurred during omeprazole solution therapy. Gastric pH was maintained above 4 on omeprazole 20 mg/day in seventy-three of seventy-five patients. No adverse events or drug interaction associated with omeprazole were encountered.

TABLE 2

| Mech Vent | Major Surgery | Multi-trauma | Head Injury | Hypo-tension | Renal Failure | Sepsis | Multiple Operation | Acid/Base | Coma | Liver Failure | Burn |
|---|---|---|---|---|---|---|---|---|---|---|---|
| 75 | 61 | 35 | 16 | 14 | 14 | 14 | 12 | 10 | 4 | 2 | 2 |

Risk factors present in patients in this study (n = 75)

TABLE 3

| | | Per day |
|---|---|---|
| RANITIDINE (day-9) | | |
| Rantidine | 150 mg/24 hr | 6.15 |
| Ancillary Product (1) | Piggyback (60%) | 0.75 |
| Ancillary Product (2) | micro tubing (etc.) | 2.00 |
| Ancillary Product (3) | filter | .40 |
| Sterile Prep required | yes | |
| R.N. time ($24/hr) | 20 minutes/day (includes pH monitoring) | 8.00 |
| R.Ph. time, hood maint. | 3 minutes ($40/hr) | 2.00 |
| Pump cost | $29/24 hrs × 50%) | 14.50 |
| TOTAL far 9 days | → | 304.20 |
| RANITIDINE Cost per day | → | 33.80 |
| CIMETIDINE (day 1–9) | | |
| Cimetidine | 900 mg/24 hr | 3.96 |
| Ancillary Product (1) | Piggyback | 1.25 |
| Ancillary Product (2) | micro tubing (etc.) | 2.00 |
| Ancillary Product (3) | filter | .40 |
| Sterile Prep required | yes | |
| R.N. time ($24/hr) | 20 minutes/day (includes pH monitoring) | 8.00 |
| R.Ph. time, hood maint. | 3 minutes ($40/hr) | 2.00 |
| Pump cost | $29/24 hrs × 50%) | 14.50 |
| TOTAL for 9 days | → | 288.99 |
| CIMETIDINE Cost per day | → | 32.11 |
| SUCRALFATE (day 1–9) | → | |
| Sucralfate | 1 Gm × 4 | 2.40 |
| Ancillary Product (1) | syringe | .20 |
| Sterile Prep required | no | |
| R.N. time ($24/hr) | 30 minutes/day (includes pH monitoring) | 12.00 |
| TOTAL for 9 days | → | 131.40 |
| SUCRALFATE Cost per day | → | 14.60 |

Note: Does not include the cost of failure and/or adverse effect.
Acquisition, preparation and delivery costs of traditional agents.

EXAMPLE X

Bacteriostatic and Fungistatic Effects of Omeprazole Solution

The antimicrobial or bacteriostatic effects of the omeprazole solution were analyzed by applicant. An omeprazole solution (2 mg/ml of 8.4% sodium bicarbonate) made according to the present invention was stored at room temperature for four weeks and then was analyzed for fungal and bacterial growth. Following four weeks of storage at room temperature, no bacterial or fungal growth was detected.

An omeprazole solution (2 mg/ml of 8.4% sodium bicarbonate) made in accordance with the present invention was stored at room temperature for twelve weeks and then was analyzed for fungal and bacterial growth. After twelve weeks of incubation at room temperature, no fungal or bacterial growth was detected.

The results of these experiments illustrate the bacteriostatic and fungistatic characteristics of the omeprazole solution of the present invention.

EXAMPLE XI

Bioequivalency Study

Healthy male and female study participants over the age of 18 will be randomized to receive omeprazole in the following forms:

(a) 20 mg of a liquid formulation of approximately 20 mg. omeprazole in 4.8.mEq sodium bicarbonate qs to 10 ml with water;

(b) 20 mg of a liquid formulation of approximately 2 mg omeprazole per 1 ml of 8.4% sodium bicarbonate.

(c) Prilosec® (omeprazole) 20 mg capsule;

(d) Capsule prepared by inserting the contents of an omeprazole 20 mg capsule into a #4 empty gelatin capsule (Lilly) uniformly dispersed in 240 mg of sodium bicarbonate powder USP to form an inner capsule. The inner capsule is then inserted into a #00 empty gelatin capsule (Lilly) together with a homogeneous mixture of 600 mg sodium bicarbonate USP and 110 mg pregelatinized starch NF.

Methodology

After appropriate screening and consent, healthy volunteers will be randomized to receive one of the following four regimens as randomly assigned by Latin Square. Each subject will be crossed to each regimen according to the randomization sequence until all subjects have received all four regimens (with one week separating each regimen).

Regimen A (20 mg omeprazole in 4.8 mEq sodium bicarbonate in 10 ml volume); Regimen B (20 mg omeprazole in 10 ml 8.4% sodium bicarbonate in 10 ml volume); Regimen C (an intact 20 mg omeprazole capsule); Regimen D (Capsule in capsule formulation, see above). For each dose/week, subjects will have an i.v. saline lock placed for blood sampling. For each regimen, blood samples will be taken over 24 hours a total of 16 times (with the last two specimens obtained 12 hours and 24 hours after drug administration).

Patient Eligibility

Four healthy females and four healthy males will be consented for the study.

Inclusion Criteria

Signed informed consent.

Exclusion Criteria

1. Currently taking $H_2$-receptor antagonist, antacid, or sucralfate.
2. Recent (within 7 days) therapy with lansoprazole, omeprazole, or other proton pump inhibitor.
3. Recent (within 7 days) therapy with warfarin.
4. History of variceal bleeding.
5. History of peptic ulcer disease or currently active G.I. bleed.
6. History of vagotomy or pyloroplasty.
7. Patient has received an investigational drug within 30 days.
8. Treatment with ketoconazole or itraconazole.
9. Patient has an allergy to omeprazole.

Pharmacokinetic Evaluation and Statistical Analysis

Blood samples will be centrifuged within 2 hours of collection and the plasma will then separated and frozen at −10° C. (or lower) until assayed. Pharmacokinetic variables will include: time to peak concentration, mean peak concentration, AUC (0-t) and (0-infinity). Analysis of variance will be used to detect statistical difference. Bioavailability will be assessed by the 90% confidence interval of the two one-sided tests on the natural logarithm of AUC.

HPLC Analysis

Omeprazole and internal standard (H168/24) will be used. Omeprazole and internal standard will be measured by modification of the procedure described by Amantea and Narang. (Amantea Mass., Narang PK. Improved Procedure for Quantification of Omeprazole and Metabolites Using Reversed-Phased High Performance Liquid Chromotography. J. Chromatography 426; 216–222. 1988). Briefly, 20 ul of omeprazole 2 mg/ml $NaHCO_3$ or Choco-Base omeprazole suspension and 190 ul of the internal standard are vortexed with 150 ul of carbonate buffer (pH=9.8), 5 ml of dichloroethane, 5 ml of hexane, and 980 ul of sterile water. After the sample is centrifuged, the organic layer is extracted and dried over a nitrogen stream. Each pellet is reconstituted with 150 ul of mobile phase (40% methanol, 52% 0.025 phosphate buffer, 8% acetonitrile, pH=7.4). Of the reconstituted sample, 75 ul is injected onto a $C_{18}$ 5 U column equilibrated with the same mobile phase at 1.1 ml/min. Under these conditions, omeprazole is eluted at approximately 5 minutes, and the internal standard at approximately 7.5 minutes. The standard curve is linear over the concentration range 0–3 mg/ml (in previous work with SOS), and the between-day coefficient of variation has been <8% at all concentrations. The typical mean R2 for the standard curve has been 0.98 in prior work with SOS (omeprazole 2 mg/ml $NaHCO_3$ 8.4%).

Applicant expects that the above experiments will demonstrate there is more rapid absorption of formulations (a), (b) and (d) as compared to the enteric coated granules of formulation (c). Additionally, applicant expects that although there will be a difference in the rates of absorption among forms (a) through (d), the extent of absorption (as measured by the area under the curve (AUC)) should be similar among the formulations (a) through (d).

EXAMPLE XII

Intraveneous PPI in Combination With Oral Parietal Cell Activator

Sixteen (16) normal, healthy male and female study subjects over the age of 18 will be randomized to receive pantoprazole as follows:

(a) 40 mg IV over 15 to 30 minutes in combination with a 20 ml oral dose of sodium bicarbonate 8.4%; and (b) 40 mg IV over 15 to 30 minutes in combination with a 20 ml oral dose of water.

The subjects will receive a single dose of (a) or (b) above, and will be crossed-over to (a) and (b) in random fashion. Serum concentrations of pantoprazole versus time after administration data will be collected, as well as. gastric pH control as measured with an indwelling pH probe.

Further, similar studies are contemplated wherein chocolate or other parietal cell activator is substituted for the parietal cell activator sodium bicarbonate, and other PPIs are substituted for pantoprazole. The parietal cell activator can be administered either within about 5 minutes before, during or within about 5 minutes after the IV dose of PPI.

Applicant expects that these studies will demonstrate that significantly less IV PPI is required to achieve therapeutic effect when it is given in combination with an oral parietal cell activator.

Additionally, administration kits of IV PPI and oral parietal cell activator can be packaged in many various forms for ease of administration and to optimize packing and shipping the product. Such kits can be in unit dose or multiple dose form.

EXAMPLE XIII

Twelve (12) Month Stability of Omeprazole Solution

A solution was prepared by mixing 8.4% sodium bicarbonate with omeprazole to produce a final concentration of 2 mg/ml to determine the stability of omeprazole solution after 12 months. The resultant preparation was stored in clear glass at room temperature, refrigerated and frozen. Samples were drawn after thorough agitation from the stored preparations at the prescribed times. The samples were then stored at 70° C. Frozen samples remained frozen until they were analyzed. When the collection process was completed, the samples were shipped to a laboratory overnight on dry ice for analysis. Samples were agitated for 30 seconds and sample aliquots were analyzed by HPLC in triplicate according to well known methods. Omeprazole and the internal standard were measured by a modification of the procedure described by Amantea and Narang. Amantea Mass., Narang PK, Improved Procedure For Quantitation Of Omeprazole And Metabolites Using Reverse-Phased High-Performance Liquid Chromatography, J. Chromatography, 426: 216–222 (1988). Twenty (20) ul of the omeprazole 2 mg/ml $NaHCO_3$ solution and 100 ul of the internal standard solution were vortexed with 150 ul of carbonate buffer (pH=9.8), 5 ml dichloroethane, 5 ml hexane, and 980 ul of sterile water. The sample was centrifuged and the organic layer was extracted and dried over a nitrogen stream. Each pellet was reconstituted with 150 ul of mobile phase (40% methanol, 52% 0.025 phosphate buffer, 8% acetonitrile, pH=7.4). Of the reconstituted sample, 75 ul were injected onto a C185u column equilibrated with the same mobile phase at 1.1 ml/min. Omeprazole was eluted at ~5 min, and the internal standard at ~7.5 min. The standard curve was linear over the concentrated range 0–3 mg/ml, and between-day coefficient of variation was <8% at all concentrations. Mean R2 for the standard curve was 0.980.

The 12 month sample showed stability at greater than 90% of the original concentration of 2 mg/ml. (i.e., 1.88 mg/ml, 1.94 mg/ml, 1.92 mg/ml).

Throughout this application various publications and patents are referenced by citation and number. The disclosure of these publications and patents in their entireties are hereby incorporated by reference into this application in order to more fully describe the state of the art to which this invention pertains.

The invention has been described in an illustrative manner, and it is to be understood the terminology used is intended to be in the nature of description rather than of limitation. Obviously, many modifications, equivalents, and variations of the present invention are possible in light of the above teachings. Therefore, it is to be understood that within the scope of the appended claims, the invention may be practiced other than as specifically described.

I claim:

1. A solid pharmaceutical composition in a dosage form that is not enteric-coated, comprising: active ingredients consisting essentially of:
   (a) a non-enteric coated proton pump inhibitor selected from the group consisting of omeprazole, lansoprazole, rabeprazole, esomeprazole, pantoprazole, pariprazole, and leminoprazole, or an enantiomer, isomer, free base, or salt thereof, in an amount of approximately 5 mg to approximately 300 mg; and
   (b) at least one buffering agent selected from the group consisting of sodium bicarbonate, potassium bicarbonate, a calcium salt, and a magnesium salt, in an amount of approximately 0.1 mEq to approximately 2.5 mEq per mg of proton pump inhibitor; wherein the dosage form is selected from the group consisting of suspension tablet, chewable tablet, effervescent powder, and effervescent tablet.

2. The composition as recited in claim 1, wherein the proton pump inhibitor is omeprazole.

3. The composition as recited in claim 1, wherein the proton pump inhibitor is lansoprazole.

4. The composition as recited in claim 1, wherein the proton pump inhibitor is rabeprazole.

5. The composition as recited in claim 1, wherein the proton pump inhibitor is esomeprazole.

6. The composition as recited in claim 1, wherein the proton pump inhibitor is pantoprazole.

7. The composition as recited in claim 1, wherein the proton pump inhibitor is pariprazole.

8. The composition as recited in claim 1, wherein the proton pump inhibitor is leminoprazole.

9. The composition as recited in claim 1, further comprising at least one flavoring agent.

10. The composition as recited in claim 1, further comprising an anti-foaming agent.

11. The composition as recited in claim 1, wherein the dosage form is a suspension tablet.

12. The composition as recited in claim 1, wherein the dosage form is a chewable tablet.

13. The composition as recited in claim 12, further comprising aspartame.

14. The composition as recited in claim 1, wherein the dosage form is an effervescent powder.

15. The composition as recited in claim 1, wherein the dosage form is an effervescent tablet.

16. The composition as recited in claim 1, wherein the buffering agent is at least about 1680 mg sodium bicarbonate.

17. The composition as recited in claim 1, wherein the buffering agent is about 1000 mg to about 1680 mg sodium bicarbonate.

18. A method of producing a liquid pharmaceutical composition, comprising: combining the composition recited in claim 11 with an aqueous medium.

19. A method of producing a liquid pharmaceutical composition, comprising: combining the composition recited in claim 12 with an aqueous medium.

20. A method of producing a liquid pharmaceutical composition, comprising: combining the composition recited in claim 14 with an aqueous medium.

21. A method of producing a liquid pharmaceutical composition, comprising: combining the composition recited in claim 15 with an aqueous medium.

22. A method for treating an acid-caused gastrointestinal disorder in a subject in need thereof, comprising: administering to the subject the dosage form of claim 1 via a route selected from the group consisting of oral, nasogastric, and gastric tube.

23. The method as recited in claim 22, wherein the disorder is selected from the group consisting of duodenal ulcer disease, gastric ulcer disease, gastroesophageal reflux disease, erosive esophagitis, poorly responsive symptomatic gastroesophageal reflux disease, pathological gastrointestinal hypersecretory disease, Zollinger Ellison Syndrome, and acid dyspepsia.

24. A method for treating an acid-caused gastrointestinal disorder in a subject in need thereof, comprising: administering to the subject a solid pharmaceutical composition in a dosage form that is not enteric-coated; wherein the composition comprises active ingredients consisting essentially of:
   (a) a therapeutically effective amount of approximately 5 mg to approximately 300 mg of a non-enteric coated proton pump inhibitor selected from the group consisting of omeprazole, lansoprazole, rabeprazole, esomeprazole, pantoprazole, pariprazole, and leminoprazole, or an enantiomer, isomer, derivative, free base, or salt thereof; and (b) a buffering agent in an amount of approximately 1.0 mEq to approximately 150 mEq selected from the group consisting of a bicarbonate salt of a group IA metal, a calcium salt, and a magnesium salt, wherein the buffering agent is in an amount sufficient to elevate gastric acid pH of the subject's stomach to prevent or inhibit gastric acid degradation of the non-enteric coated proton pump inhibitor and achieve sufficient bioavailability of the proton pump inhibitor in the subject to elicit a therapeutic effect.

25. The method of claim 24, wherein the calcium salt is selected from the group consisting of calcium acetate, calcium glycerophosphate, calcium chloride, calcium hydroxide, calcium lactate, calcium bicarbonate, calcium gluconate, and other calcium salts.

26. The method of claim 24, wherein the sodium bicarbonate is in an amount from about 1000 mg to about 1680 mg.

27. The method of claim 24, wherein the sodium bicarbonate is in an amount of at least about 1680 mg.

28. The method of claim 24, wherein the calcium salt is calcium carbonate present in an amount from about 250 mg to about 1000 mg.

29. The method of claim 24, wherein the calcium salt is calcium carbonate present in an amount from about 500 mg to about 1000 mg.

30. The method of claim 24, wherein the calcium salt is calcium carbonate present in an amount of at least about 1000 mg.

31. The method of claim 24, wherein the buffering agent is in an amount of at least 10 mEq.

32. The method of claim 24, wherein the buffering agent is in an amount from about 10 mEq to about 70 mEq.

33. The method of claim 24, wherein the buffering agent is in an amount from about 20 mEq to about 40 mEq.

34. The method of claim 24, wherein the proton pump inhibitor is in an amount from about 10 mg to about 100 mg.

35. The method of claim 24, wherein the proton pump inhibitor is omeprazole.

36. The method of claim 35, wherein the omeprazole is present in an amount of about 10 mg.

37. The method of claim 35, wherein the omeprazole is present in an amount of about 20 mg.

38. The method of claim 35, wherein the omeprazole is present in an amount of about 40 mg.

39. The method of claim 35, wherein the omeprazole is present in an amount of about 60 mg.

40. The method of claim 35, wherein the omeprazole is present in an amount of about 80 mg.

41. The method of claim 35, wherein the omeprazole is present in an amount of about 100 mg.

42. The method of claim 24, wherein the proton pump inhibitor is lansoprazole.

43. The method of claim 42, wherein the lansoprazole is present in an amount of about 15 mg.

44. The method of claim 42, wherein the lansoprazole is present in an amount of about 30 mg.

45. The method of claim 42, wherein the lansoprazole is present in an amount of about 45 mg.

46. The method of claim 42, wherein the lansoprazole is present in an amount of about 60 mg.

47. The method of claim 42, wherein the lansoprazole is present in an amount of about 90 mg.

48. The method of claim 42, wherein the lansoprazole is present in an amount of about 100 mg.

49. The method of claim 24, wherein the proton pump inhibitor is micronized.

50. The method of claim 24, wherein the composition is in a dosage form selected from the group consisting of a tablet, powder, suspension tablet, chewable tablet, capsule, effervescent powder, effervescent tablet, pellets, and granules.

51. The method of claim 24, wherein the subject is a human.

52. The method of claim 24, wherein the dosage form further comprises a flavoring agent.

53. The method of claim 52, wherein the flavoring agent comprises aspartame, chocolate, root beer, peppermint, spearmint, or watermelon, and combinations of any of the foregoing.

54. The method of claim 24, wherein the composition is provided as a separate component of a kit.

55. The method of claim 24, wherein the disorder is selected from the group consisting of duodenal ulcer disease, gastric ulcer disease, gastroesophageal reflux disease, erosive esophagitis, poorly responsive symptomatic gastroesophageal reflux disease, pathological gastrointestinal hypersecretory disease, Zollinger Ellison Syndrome, and acid dyspepsia.

56. The method of claim 24, wherein the dosage form is administered once or twice a day.

57. A solid pharmaceutical composition in a dosage form that is not enteric-coated, comprising: active ingredients consisting essentially of:

(a) a therapeutically effective amount of a non-enteric coated proton pump inhibitor selected from the group consisting of omeprazole, lansoprazole, rabeprazole, esomeprazole, pantoprazole, pariprazole, and leminoprazole, or an enantiomer, isomer, derivative, free base, or salt thereof; and (b) a buffering agent selected from the group consisting of sodium bicarbonate, and calcium carbonate, in an amount more than about 40 times the amount of the proton pump inhibitor on a weight to weight basis in the composition.

58. The composition as recited in claim 57, wherein the buffering agent is sodium bicarbonate.

59. The composition as recited in claim 57, wherein the sodium bicarbonate is in an amount from about 400 mg to about 4000 mg.

60. The composition as recited in claim 57, wherein the sodium bicarbonate is in an amount of at least about 800 mg.

61. The composition as recited in claim 57, wherein the buffering agent is calcium carbonate.

62. The composition as recited in claim 57, wherein the calcium carbonate is in an amount from about 400 mg to about 4000 mg.

63. The composition as recited in claim 61, wherein the calcium carbonate is in an amount from about 500 mg to about 1000 mg.

64. The composition as recited in claim 61, wherein the calcium carbonate is in an amount of at least about 800 mg.

65. The composition as recited in claim 57, wherein the proton pump inhibitor is in an amount from about 10 mg to about 100 mg.

66. The composition as recited in claim 57, wherein the proton pump inhibitor is omeprazole.

67. The composition as recited in claim 66, wherein the omeprazole is present in an amount of about 10 mg.

68. The composition as recited in claim 66, wherein the omeprazole is present in an amount of about 20 mg.

69. The composition as recited in claim 66, wherein the omeprazole is present in an amount of about 40 mg.

70. The composition as recited in claim 66, wherein the omeprazole is present in an amount of about 60 mg.

71. The composition as recited in claim 66, wherein the omeprazole is present in an amount of about 80 mg.

72. The composition as recited in claim 66, wherein the omeprazole is present in an amount of about 100 mg.

73. The composition as recited in claim 57, wherein the proton pump inhibitor is lansoprazole.

74. The composition as recited in claim 73, wherein the lansoprazole is present in an amount of about 15 mg.

75. The composition as recited in claim 73, wherein the lansoprazole is present in an amount of about 30 mg.

76. The composition as recited in claim 73, wherein the lansoprazole is present in an amount of about 45 mg.

77. The composition as recited in claim 73, wherein the lansoprazole is present in an amount of about 60 mg.

78. The composition as recited in claim 73, wherein the lansoprazole is present in an amount of about 90 mg.

79. The composition as recited in claim 73, wherein the lansoprazole is present in an amount of about 100 mg.

80. The composition as recited in claim 57, wherein the proton pump inhibitor is micronized.

81. The composition as recited in claim 57, wherein the composition is in a dosage form selected from the group consisting of a tablet, powder, suspension tablet, chewable tablet, capsule, effervescent powder, effervescent tablet, pellets, and granules.

82. The composition as recited in claim 57, further comprising a flavoring agent comprising aspartame, chocolate, root beer, peppermint, spearmint, or watermelon, and combinations of any of the foregoing.

83. The composition as recited in claim 57, wherein the amount of the buffering agent is more than about 50 times the amount of the proton pump inhibitor on a weight to weight basis in the composition.

84. The composition as recited in claim 57, wherein the amount of the buffering agent is more than about 60 times the amount of the proton pump inhibitor on a weight to weight basis in the composition.

85. The composition as recited in claim 57, wherein the amount of the buffering agent is more than about 70 times the amount of the proton pump inhibitor on a weight to weight basis in the composition.

86. The composition as recited in claim 57, wherein the amount of the buffering agent is more than about 80 times the amount of the proton pump inhibitor on a weight to weight basis in the composition.

87. The composition as recited in claim 57, wherein the amount of the buffering agent is more than about 90 times the amount of the proton pump inhibitor on a weight to weight basis in the composition.

88. The composition as recited in claim 57, wherein the amount of the buffering agent is more than about 100 times the amount of the proton pump inhibitor on a weight to weight basis in the composition.

89. The composition as recited in claim 57, wherein the composition is provided as a separate component of a kit.

90. A method of producing a liquid pharmaceutical composition comprising: combining the dosage form of claim 57 with an aqueous medium.

91. A method for treating an acid-caused gastrointestinal disorder in a subject in need thereof, comprising: administering to the subject the dosage form as recited in claim 57 via a route selected from the group consisting of oral, nasogastric, and gastric tube.

92. The method as recited in claim 91, wherein the disorder is selected from the group consisting of duodenal ulcer disease, gastric ulcer disease, gastroesophageal reflux disease, erosive esophagitis, poorly responsive symptomatic gastroesophageal reflux disease, pathological gastrointestinal hypersecretory disease, Zollinger Ellison Syndrome, and acid dyspepsia.

93. The method as recited in claim 91, wherein the composition is administered once or twice a day.

94. A method for administering a liquid pharmaceutical composition to a subject, comprising: combining the pharmaceutical composition as recited in claim 57 with an aqueous medium to form a suspension, and orally administering the suspension to the subject in a single dose without administering an additional buffering agent.

95. The composition as recited in claim 1, wherein the proton pump inhibitor is in an amount from about 10 mg to about 100 mg.

96. The composition as recited in claim 95, wherein the proton pump inhibitor is omeprazole.

97. The composition as recited in claim 95, wherein the omeprazole is present in an amount of about 10 mg.

98. The composition as recited in claim 95, wherein the omeprazole is present in an amount of about 20 mg.

99. The composition as recited in claim 95, wherein the omeprazole is present in an amount of about 40 mg.

100. The composition as recited in claim 95, wherein the omeprazole is present in an amount of about 60 mg.

101. The composition as recited in claim 95, wherein the omeprazole is present in an amount of about 80 mg.

102. The composition as recited in claim 95, wherein the omeprazole is present in an amount of about 100 mg.

103. The composition as recited in claim 95, wherein the proton pump inhibitor is lansoprazole.

104. The composition as recited in claim 103, wherein the lansoprazole is present in an amount of about 15 mg.

105. The composition as recited in claim 103, wherein the lansoprazole is present in an amount of about 30 mg.

106. The composition as recited in claim 103, wherein the lansoprazole is present in an amount of about 45 mg.

107. The composition as recited in claim 103, wherein the lansoprazole is present in an amount of about 60 mg.

108. The composition as recited in claim 103, wherein the lansoprazole is present in an amount of about 90 mg.

109. The composition as recited in claim 103, wherein the lansoprazole is present in an amount of about 100 mg.

110. The composition as recited in claim 1, wherein the proton pump inhibitor is micronized.

111. The composition as recited in claim 9, wherein the flavoring agent comprises aspartame, chocolate, root beer, peppermint, spearmint, or watermelon, and combinations of any of the foregoing.

112. The composition as recited in claim 1, wherein the composition is provided as a separate component of a kit.

113. The composition of claim 1, wherein the buffering agent comprises a bicarbonate salt of a Group IA metal.

114. The composition of claim 1, wherein the buffering agent comprises at least one of magnesium hydroxide, magnesium lactate, magnesium gluconate, magnesium oxide, magnesium carbonate, or magnesium silicate.

115. The composition of claim 1, wherein the buffering agent comprises at least one of calcium acetate, calcium glycerophosphate, calcium chloride, calcium hydroxide, calcium lactate, calcium carbonate, calcium bicarbonate, calcium gluconate, or other calcium salts.

116. The composition of claim 1, further comprising a disintegrant, flow aid, lubricant, adjuvant excipient, colorant, diluent, moistening agent, preservative, and pharmaceutically compatible carrier.

117. The method of claim 24, wherein the composition further comprises a disintegrant, flow aid, lubricant, adjuvant, excipient, colorant, diluent, moistening agent, preservative, and pharmaceutically compatible carrier.

118. The composition of claim 57, further comprising a disintegrant, flow aid, lubricant, adjuvant, excipient, colorant, diluent, moistening agent, preservative, and pharmaceutically compatible carrier.

* * * * *

UNITED STATES PATENT AND TRADEMARK OFFICE
CERTIFICATE OF CORRECTION

PATENT NO. : 6,489,346 B1
DATED : December 3, 2002
INVENTOR(S) : Phillips, J.O.

It is certified that error appears in the above-identified patent and that said Letters Patent is hereby corrected as shown below:

Column 2,
Line 17, delete "cimetidine" and insert -- Cimetidine --, therefor.
Line 19, delete "39" and insert -- 30 --, therefor.
Lines 41 and 63, delete "64" and insert -- 84 --, therefor.
Line 48, delete "Antacids" and insert -- antacids --, therefor.

Column 9,
Line 42, delete "Brunton" and insert -- Goodman AG, et al. --, therefor.
Lines 43-44, delete "In Goodman A G, et al." and insert -- in --, therefor.

Column 13,
Line 31, delete "inhibitor" and insert -- inhibitors --, therefor.

Column 20,
Lines 32-33, after "Dextrose 10 mg" insert a new line as follows: -- Calcium Hydroxide 10 mg --

Column 22,
Lines 51-52, delete "Choco-Base," and insert -- Choco-BaseTM --, therefor.
Line 56, delete "Choco-Base" and insert -- Choco-BaseTM --, therefor.

Column 23,
Line 29, after "males and 6" insert -- were --, therefor.

Column 24,
Line 21, delete "Choco-Base" and insert -- Choco-BaseTM --, therefor.

Column 28,
Lines 39, 46 and 55, delete "Choco-Base" and insert -- Choco-BaseTM --, therefor.

Column 36,
Line 30, after "TOTAL", delete "far" and insert -- for --, therefor.

UNITED STATES PATENT AND TRADEMARK OFFICE
CERTIFICATE OF CORRECTION

PATENT NO.     : 6,489,346 B1
DATED          : December 3, 2002
INVENTOR(S)    : Phillips, J.O.

It is certified that error appears in the above-identified patent and that said Letters Patent is hereby corrected as shown below:

Column 36 (cont'd),
Line 51, after Table 3, please insert Tables 4 and 5 as follows:

TABLE 4

The average length of treatment was 9 days. Cost of care was calculated from these days.

| | | Per Day | Total |
|---|---|---|---|
| OMEPRAZOLE (day 1) | | | |
| Product acquisition cost | 40 mg load x 2 5.66/dose) | 11.32 | 11.32 |
| Ancillary product | materials for solution preparation | 0.41 | 0.41 |
| Ancillary product | syringe w/needle | 0.20 | 0.40 |
| Sterile preparation required | no | | |
| SOS preparation time (R.N.) | 6 minutes | 2.40 | 4.80 |
| R.N. time ($24/hr) | 21 minutes/day (includes pH monitoring) | 8.40 | 8.40 |
| OMEPRAZOLE (days 2-9) | | | |
| Product acquisition cost | 20 mg per day | 2.80 | 22.65 |
| Ancillary product | materials for solution preparation | 0.41 | 0.82 |
| Ancillary product | syringe w/needle | 0.20 | 1.60 |
| Sterile preparation required | no | | |
| SOS preparation time (R.N.) | 6 minutes | 2.40 | 4.80 |
| R.N. time ($24/hr) | 18 minutes/day (includes pH monitoring) | 8.40 | 57.60 |
| 2/75 patient require 40 mg simplified omeprazole solution per day (days 2-9) | | | 0.63 |
| No additional cost for adverse effects or for failure | | | |
| TOTAL | | 113.43 | |
| Simplified Omeprazole Solution cost per day | | 12.60 | |

Pharmacoeconomic evaluation of omeprazole cost of care

TABLE 5

| Time | Control | 1 hour | 24 hour | 2 day | 7 day | 14 day |
|---|---|---|---|---|---|---|
| Conc (mg/ml) | 2.01 | 2.07 | 1.94 | 1.96 | 1.97 | 1.98 |

Stability of Simplified Omeprazole Solution at room temperature (25° C.). Values are the mean of three samples.--

Column 37,
Line 14, delete "bicarbonate." and insert -- bicarbonate; --, therefor.
Line 63, after "plasma will then", insert -- be --, therefor.

Column 38,
Line 11, delete "Choco-Base" and insert -- Choco-BaseTM --, therefor.
Line 12, after "suspension and", delete "190" and insert -- 100 --, therefor.

UNITED STATES PATENT AND TRADEMARK OFFICE
CERTIFICATE OF CORRECTION

PATENT NO. : 6,489,346 B1
DATED : December 3, 2002
INVENTOR(S) : Phillips, J.O.

It is certified that error appears in the above-identified patent and that said Letters Patent is hereby corrected as shown below:

Column 39,
Line 22, after "suspension and", delete "190" and insert -- 100 --, therefor.
Line 59, after "an enantiomer, isomer," insert -- derivative, --, therefor.

Signed and Sealed this

Twenty-eighth Day of December, 2004

JON W. DUDAS
*Director of the United States Patent and Trademark Office*